US010124500B2

(12) United States Patent
Whited et al.

(10) Patent No.: US 10,124,500 B2
(45) Date of Patent: Nov. 13, 2018

(54) CAM-ACTUATED SPLIT BLADE HOUSING FOR POWER OPERATED ROTARY KNIFE

(71) Applicant: Bettcher Industries, Inc., Birmingham, OH (US)

(72) Inventors: Jeffrey A. Whited, Amherst, OH (US); Dennis R. Seguin, Jr., Elyria, OH (US)

(73) Assignee: Bettcher Industries, Inc., Birmingham, OH (US)

( * ) Notice: Subject to any disclaimer, the term of this patent is extended or adjusted under 35 U.S.C. 154(b) by 0 days.

(21) Appl. No.: 15/822,914

(22) Filed: Nov. 27, 2017

(65) Prior Publication Data

US 2018/0162002 A1    Jun. 14, 2018

Related U.S. Application Data

(63) Continuation-in-part of application No. 15/374,207, filed on Dec. 9, 2016.

(51) Int. Cl.
*B26B 25/00* (2006.01)
*A61B 17/322* (2006.01)
(Continued)

(52) U.S. Cl.
CPC ............ *B26B 25/002* (2013.01); *A22C 17/04* (2013.01); *A61B 17/322* (2013.01); *A61B 2090/033* (2016.02); *B26B 7/005* (2013.01)

(58) Field of Classification Search
CPC .. B26B 25/002; B26B 7/005; A61B 2090/033
See application file for complete search history.

(56) References Cited

U.S. PATENT DOCUMENTS

| 1,220,345 A | 3/1917 | Koster |
| 1,374,988 A | 4/1921 | Cooper |

(Continued)

FOREIGN PATENT DOCUMENTS

| CA | 2796222 | 10/2011 |
| CA | 2883924 | 3/2014 |

(Continued)

OTHER PUBLICATIONS

Oct. 3, 2011 Decision and Opinion of the United States Court of Appeals for the Federal Circuit (Appeal No. 2011-1038,-1046) regarding the case styled *Bettcher Industries, Inc. v. Bunzl USA, Inc. and Bunzl Processor Distribution, LLC*, Case No. 3:08 CV 2423, U.S. District Court for the Northern District of Ohio, Judge Zouhary. The Decision and Opinion relates to U.S. Pat. No. 7,000,325, (47 pages).

(Continued)

*Primary Examiner* — Sean Michalski
(74) *Attorney, Agent, or Firm* — Tarolli, Sundheim, Covell & Tummino LLP

(57) ABSTRACT

A blade housing assembly for a power operated rotary knife including a split blade housing and a cam mechanism actuatable for changing a blade housing diameter between a blade supporting position and a blade changing position. The blade housing including an annular blade support section, a mounting section and a radially extending split extending through the mounting section and an inner wall of the blade support section and defining a split distance between first and second circumferential ends of the inner wall. The mounting section includes a first body portion and a second body portion on opposite sides of the radially extending split. The cam mechanism includes a cam plate bridging the first and second body portions and a cam member rotatably supported by the cam plate. The cam member is rotatable (Continued)

between a first, closed position and a second, open position to change the blade housing diameter.

20 Claims, 19 Drawing Sheets

(51) Int. Cl.
 *A22C 17/04* (2006.01)
 *A61B 90/00* (2016.01)
 *B26B 7/00* (2006.01)

(56) References Cited

U.S. PATENT DOCUMENTS

| | | | |
|---|---|---|---|
| 1,476,345 A | 12/1923 | McGee | |
| 1,966,266 A | 7/1934 | Skelly | |
| 2,266,888 A | 12/1941 | McCurdy et al. | |
| 2,656,012 A | 10/1953 | Thorpe | |
| 2,827,657 A | 3/1958 | Bettcher | |
| 3,024,532 A | 3/1962 | Bettcher | |
| 3,150,409 A | 9/1964 | Wilcox | |
| RE25,947 E | 12/1965 | Bettcher | |
| 3,269,010 A * | 8/1966 | Bettcher | B26B 25/002 30/276 |
| 3,349,485 A | 10/1967 | Bettcher | |
| 3,461,557 A | 8/1969 | Behring | |
| 3,512,519 A | 5/1970 | Hall | |
| 3,592,519 A | 7/1971 | Martin | |
| 3,688,403 A | 9/1972 | Bettcher | |
| 3,816,875 A | 6/1974 | Duncan et al. | |
| 3,852,882 A | 12/1974 | Bettcher | |
| 4,082,232 A | 4/1978 | Brewer | |
| 4,170,063 A | 10/1979 | Bettcher | |
| 4,178,683 A * | 12/1979 | Bettcher | B26B 25/002 30/276 |
| 4,198,750 A | 4/1980 | Bettcher | |
| 4,236,531 A | 12/1980 | McCullough | |
| 4,267,759 A | 5/1981 | Sullivan et al. | |
| 4,326,361 A | 4/1982 | McGill | |
| 4,336,651 A * | 6/1982 | Caro | B26B 25/002 30/49 |
| 4,363,170 A * | 12/1982 | McCullough | B26B 25/002 30/276 |
| 4,418,591 A | 12/1983 | Astle | |
| 4,439,924 A | 4/1984 | Bettcher | |
| 4,492,027 A | 1/1985 | Bettcher | |
| 4,494,311 A * | 1/1985 | McCullough | B26B 25/002 30/276 |
| 4,509,261 A | 4/1985 | Bettcher | |
| 4,516,323 A | 5/1985 | Bettcher | |
| 4,575,937 A * | 3/1986 | McCullough | B26B 25/002 30/276 |
| 4,575,938 A * | 3/1986 | McCullough | B26B 25/002 30/276 |
| 4,590,576 A * | 5/1986 | Elpiner | G05D 7/0635 137/624.11 |
| 4,590,676 A | 5/1986 | Bettcher | |
| 4,609,227 A | 9/1986 | Wild et al. | |
| 4,637,140 A | 1/1987 | Bettcher | |
| 4,829,860 A | 5/1989 | VanderPol | |
| 4,854,046 A * | 8/1989 | Decker | B26B 25/002 30/264 |
| 4,858,321 A * | 8/1989 | McCullough | B26B 25/002 30/276 |
| 4,865,473 A * | 9/1989 | De Vito | F16C 33/4635 384/572 |
| 4,909,640 A | 3/1990 | Nakanishi | |
| 4,942,665 A * | 7/1990 | McCullough | A22C 17/04 30/276 |
| 5,031,323 A * | 7/1991 | Honsa | B25F 5/021 30/276 |
| 5,033,876 A * | 7/1991 | Kraus | F16C 19/463 384/572 |
| 5,071,264 A | 12/1991 | Franke et al. | |
| 5,099,721 A | 3/1992 | Decker et al. | |
| 5,230,154 A * | 7/1993 | Decker | B26B 25/002 16/422 |
| 5,331,877 A | 7/1994 | Ishii | |
| 5,419,619 A | 5/1995 | Lew | |
| 5,484,331 A | 1/1996 | Buhlke | |
| 5,499,492 A * | 3/1996 | Jameson | A01D 34/003 239/282 |
| 5,522,142 A * | 6/1996 | Whited | B26B 25/002 30/276 |
| 5,529,532 A | 6/1996 | Desrosiers | |
| 5,582,041 A * | 12/1996 | Spiess | C14B 19/00 30/276 |
| 5,664,332 A * | 9/1997 | Whited | B26B 25/002 30/276 |
| 5,692,307 A | 12/1997 | Whited | |
| 5,743,659 A | 4/1998 | Stewart | |
| 5,749,661 A | 5/1998 | Moller | |
| 5,761,817 A | 6/1998 | Whited | |
| 5,940,972 A | 8/1999 | Baris | |
| 5,971,413 A | 10/1999 | El-Kassouf | |
| 6,247,847 B1 * | 6/2001 | Lob | F16C 19/26 384/51 |
| 6,354,949 B1 | 3/2002 | Baris et al. | |
| 6,364,086 B1 * | 4/2002 | Blaurock | F16C 33/3825 193/35 MD |
| 6,604,288 B2 | 8/2003 | Whited et al. | |
| 6,615,494 B2 | 9/2003 | Long et al. | |
| 6,634,257 B2 | 10/2003 | Long | |
| 6,655,033 B2 | 12/2003 | Hermann et al. | |
| 6,662,452 B2 | 12/2003 | Whited | |
| 6,665,940 B2 * | 12/2003 | Sanders | A01D 34/90 30/276 |
| 6,694,649 B2 | 2/2004 | Whited et al. | |
| 6,751,872 B1 * | 6/2004 | Whited | B26B 25/002 30/276 |
| 6,769,184 B1 | 8/2004 | Whited | |
| 6,857,191 B2 | 2/2005 | Whited et al. | |
| 6,938,348 B2 | 9/2005 | Roncaglia | |
| 6,978,548 B2 | 12/2005 | Whited et al. | |
| 7,000,325 B2 * | 2/2006 | Whited | B26B 25/002 30/276 |
| 7,107,887 B2 | 9/2006 | Whited | |
| 7,207,114 B2 | 4/2007 | Rosu et al. | |
| 7,340,840 B2 | 3/2008 | Whited | |
| 8,074,363 B2 | 12/2011 | Whited | |
| 8,448,340 B2 | 5/2013 | Whited | |
| 8,505,207 B2 | 8/2013 | Thien | |
| 8,661,692 B2 | 3/2014 | Whited | |
| 8,671,580 B2 | 3/2014 | Whited | |
| 8,695,222 B2 | 4/2014 | Whited | |
| 8,726,524 B2 | 5/2014 | Whited et al. | |
| 8,739,416 B2 | 6/2014 | Mascari | |
| 8,745,881 B2 | 6/2014 | Thompson | |
| 8,806,761 B2 | 8/2014 | Whited | |
| 8,950,076 B2 | 2/2015 | Whited | |
| 8,968,107 B2 | 3/2015 | Rapp | |
| 9,089,980 B2 | 7/2015 | Whited | |
| 9,121,438 B2 | 9/2015 | Mascari | |
| 9,186,171 B2 | 11/2015 | Esarey | |
| 9,211,183 B2 | 12/2015 | Whited | |
| 9,211,650 B2 | 12/2015 | Mascari | |
| 9,227,332 B2 | 1/2016 | Thompson | |
| 9,265,263 B2 | 2/2016 | Whited | |
| 9,364,962 B2 | 6/2016 | Whited | |
| 9,452,541 B2 | 9/2016 | Mascari | |
| 9,475,203 B2 | 10/2016 | Whited et al. | |
| 9,522,473 B2 | 12/2016 | Mascari | |
| 9,573,283 B2 | 2/2017 | Thompson | |
| 9,579,810 B2 | 2/2017 | Mascari | |
| 9,592,076 B2 | 3/2017 | Esarey | |
| 9,623,577 B2 | 4/2017 | Whited | |
| 9,833,919 B2 | 12/2017 | Mascari | |
| 2003/0070301 A1 | 4/2003 | Hermann | |
| 2003/0084576 A1 | 5/2003 | Whited | |
| 2003/0131482 A1 * | 7/2003 | Long | A22B 5/165 30/276 |
| 2003/0196333 A1 | 10/2003 | Whited | |

(56) References Cited

U.S. PATENT DOCUMENTS

| | | |
|---|---|---|
| 2004/0134326 A1 | 7/2004 | Long |
| 2005/0126015 A1 | 6/2005 | Whited |
| 2005/0217119 A1* | 10/2005 | Rapp .................. A22B 5/165 30/276 |
| 2006/0037200 A1* | 2/2006 | Rosu .................. B26B 25/002 30/276 |
| 2006/0137193 A1 | 6/2006 | Whited |
| 2006/0211966 A1 | 9/2006 | Hatton |
| 2007/0283573 A1 | 12/2007 | Levsen |
| 2007/0283574 A1* | 12/2007 | Levsen .................. A22B 5/165 30/276 |
| 2008/0022537 A1* | 1/2008 | Clarke .................. B23D 45/16 30/390 |
| 2008/0078158 A1 | 4/2008 | Reist |
| 2008/0098605 A1* | 5/2008 | Whited .................. B26B 25/002 30/276 |
| 2009/0227192 A1 | 9/2009 | Luthi et al. |
| 2010/0101097 A1* | 4/2010 | Thien .................. B26B 25/002 30/276 |
| 2010/0111460 A1 | 5/2010 | Albrecht |
| 2010/0170097 A1* | 7/2010 | Levsen .................. A22B 5/165 30/276 |
| 2011/0185580 A1* | 8/2011 | Whited .................. A22B 5/165 30/276 |
| 2011/0247220 A1* | 10/2011 | Whited .................. B26B 25/002 30/276 |
| 2012/0011980 A1 | 1/2012 | Kroger |
| 2012/0030952 A1 | 2/2012 | Levsen |
| 2013/0025134 A1 | 1/2013 | Mascari |
| 2013/0025136 A1 | 1/2013 | Whited |
| 2013/0025137 A1 | 1/2013 | Whited |
| 2013/0025138 A1 | 1/2013 | Whited |
| 2013/0025139 A1 | 1/2013 | Whited |
| 2013/0056324 A1* | 3/2013 | Freund .................. A22B 5/0029 192/69 |
| 2013/0104404 A1* | 5/2013 | Levsen .................. A22C 17/12 30/276 |
| 2013/0185944 A1 | 7/2013 | Thompson et al. |
| 2013/0205572 A1* | 8/2013 | Mascari .................. F16C 1/02 29/515 |
| 2013/0243358 A1 | 9/2013 | Stork |
| 2013/0266250 A1 | 10/2013 | Brown |
| 2013/0326886 A1* | 12/2013 | Levsen .................. B26B 25/002 30/276 |
| 2014/0074118 A1* | 3/2014 | Esarey .................. A61B 17/322 606/132 |
| 2014/0074120 A1 | 3/2014 | Esarey |
| 2015/0377289 A1 | 12/2015 | Scheidel |
| 2016/0082612 A1 | 3/2016 | Mascari |
| 2016/0279818 A1 | 9/2016 | Whited |
| 2016/0345996 A1 | 12/2016 | Esarey |

FOREIGN PATENT DOCUMENTS

| | | |
|---|---|---|
| DE | 19958802 | 7/2001 |
| EP | 0689905 | 1/1996 |
| EP | 0816026 | 1/1998 |
| EP | 1226907 | 7/2002 |
| EP | 1356902 | 10/2003 |
| EP | 1403012 | 8/2004 |
| EP | 1527584 | 5/2005 |
| EP | 1527853 | 5/2005 |
| EP | 1916075 | 4/2008 |
| EP | 2353805 | 8/2011 |
| EP | 2497366 | 9/2012 |
| EP | 2557935 | 6/2016 |
| EP | 2736684 | 1/2017 |
| FR | 1216947 | 4/1960 |
| JP | 2000052293 | 2/2000 |
| WO | WO 0124977 | 4/2001 |
| WO | WO 01/41980 | 6/2001 |
| WO | WO 2008/107490 | 9/2008 |
| WO | WO 2011/130057 | 10/2011 |
| WO | WO 2013/016019 | 1/2013 |
| WO | WO 2013/016020 | 1/2013 |
| WO | WO 2013/016021 | 1/2013 |
| WO | WO 2013/016022 | 1/2013 |
| WO | WO 2013/016024 | 1/2013 |
| WO | WO 2013/016344 | 1/2013 |
| WO | WO 2014/039601 | 3/2014 |
| WO | WO 2014/039609 | 3/2014 |
| WO | WO 2014/159349 | 10/2014 |
| WO | WO 2014/160043 | 10/2014 |

OTHER PUBLICATIONS

International Search Report and Written Opinion of the International Searching Authority dated Feb. 14, 2018 for PCT International Application No. PCT/US2017/064500, Filed Dec. 4, 2017. PCT International Application No. PCT/US2017/064500 claims priority from U.S. Appl. No. 15/374,207, filed Dec. 9, 2016. The present application (U.S. Appl. No. 15/822,914) is a continuation-in-part of and claims priority from U.S. Appl. No. 15/374,207, (13 pages).

International Search Report and Written Opinion of the International Searching Authority dated Jul. 13, 2018 for PCT International Application No. PCT/US2018/036498, filed Jun. 7, 2018. PCT International Application No. PCT/US2018/036498 corresponds to and claims priority from the present application. (6 pages).

* cited by examiner

CAM-ACTUATED SPLIT BLADE HOUSING FOR POWER OPERATED ROTARY KNIFE

CROSS-REFERENCE TO RELATED APPLICATION

The present application is a continuation-in-part application of co-pending U.S. application Ser. No. 15/374,207, filed Dec. 9, 2016 and entitled POWER OPERATED ROTARY KNIFE, The present application claims priority from above-identified application Ser. No. 15/374,207, which is incorporated herein in its entirety by reference, for any and all purposes.

TECHNICAL FIELD

The present disclosure relates to a power operated rotary knife and, more specifically, to a split blade housing assembly for a power operated rotary knife that includes a split blade housing and a two-position cam mechanism that, in a first, closed position of the cam mechanism, holds or secures the split blade housing in a first, blade-supporting position, and, in a second, open position of the cam mechanism, secures the split blade housing in a second, blade changing position.

BACKGROUND

Hand held, power operated rotary knives are widely used in meat processing facilities for meat cutting and trimming operations. Power operated rotary knives also have application in a variety of other industries where cutting and/or trimming operations need to be performed quickly and with less effort than would be the case if traditional manual cutting or trimming tools were used, e.g., long knives, scissors, nippers, etc. By way of example, power operated rotary knives may be effectively utilized for such diverse tasks as tissue harvesting or recovery, debriding/removal of skin tissue, bone tissue, tendon/ligament harvesting from human or animal tissue donors for medical purposes. Power operated rotary knives may also be used for taxidermy and for cutting and trimming of elastomeric or urethane foam for a variety of applications including vehicle seats.

Power operated rotary knives typically include a handle assembly and a head assembly attachable to the handle assembly. The head assembly includes an annular blade housing and an annular rotary knife blade supported for rotation by the blade housing. The annular rotary blade of conventional power operated rotary knives is typically rotated by a drive assembly which include a flexible shaft drive assembly extending through an opening in the handle assembly. The shaft drive assembly engages and rotates a pinion gear supported by the head assembly. The flexible shaft drive assembly includes a stationary outer sheath and a rotatable interior drive shaft which is driven by an electric motor. Alternatively, the pinion gear may be driven by a pneumatic motor mounted within the handle assembly. Gear teeth of the pinion gear engage mating gear teeth formed on an upper surface of the rotary knife blade.

Upon rotation of the pinion gear by the drive shaft of the flexible shaft drive assembly, the annular rotary blade rotates within the blade housing at a high RPM, on the order of 900-1900 RPM, depending on the structure and characteristics of the drive assembly including the motor, the shaft drive assembly, and a diameter and the number of gear teeth formed on the rotary knife blade. Power operated rotary knives are disclosed in U.S. Pat. Nos. 6,354,949 to Baris et al., 6,751,872 to Whited et al., 6,769,184 to Whited, 6,978, 548 to Whited et al., 8,448,340 to Whited, and 8,726,524 to Whited et al., all of which are assigned to the assignee of the present invention and all of which are incorporated herein in their respective entireties by reference.

SUMMARY

In one aspect, the present disclosure relates to a blade housing assembly for supporting an annular rotary knife blade of a power operated rotary knife for rotation about a central axis of rotation, the blade housing assembly comprising: a split blade housing including: an annular blade support section, an inner wall of the blade support section defining a blade bearing region; a mounting section extending from the blade support section; and a radially extending split extending through the mounting section and the inner wall of the blade support section and defining a split distance between first and second circumferential ends of the inner wall; the mounting section including a first body portion and a second body portion on opposite sides of the radially extending split, the first body portion including a first surface and axially spaced apart second surface including a first cam slot extending transversely with respect to the radially extending split and having a first end portion and a spaced apart second end portion; and a cam mechanism including: a cam plate bridging the first and second body portions of the mounting section of the split blade housing; and a cam member rotatably supported by the cam plate, the cam member rotatable between a first, closed position and a second, open position and including a base having a first cam pin extending from a first surface of the base and received in the first cam slot of the first body portion of the mounting section of the split blade housing, in the first, closed position of the cam member, the first cam pin is positioned nearer the first end portion of the first cam slot and the split distance between the first and second circumferential ends of the inner wall being a first value, in the second, open position of the cam member, the first cam pin is positioned nearer the second end portion of the first cam slot and the split distance between the first and second circumferential ends of the inner wall being a second value, the second value being greater than the first value.

In another aspect, the present disclosure relates to a blade housing assembly for supporting an annular rotary knife blade of a power operated rotary knife for rotation about a central axis of rotation, the blade housing assembly comprising: a split blade housing including: an annular blade support section having an inner wall and a radially spaced apart outer wall and a first end and an axially spaced apart second end, the inner wall of the blade support section defining a blade bearing region; a mounting section extending from the blade support section; and a radially extending split extending through the mounting section and the inner wall of the blade support section and defining a split distance between first and second circumferential ends of the inner wall; the mounting section including a first body portion and a second body portion on opposite sides of the radially extending split, the first body portion including a first surface and an axially spaced apart second surface including a first cam slot extending transversely with respect to the radially extending split and having a first end portion and a spaced apart second end portion, the second body portion including a first surface and an axially spaced apart second surface including a second cam slot extending transversely with respect to the radially extending split and having a first end portion and a spaced apart second end portion; and a cam mechanism including: a cam plate bridging the first and second body portions of the mounting section of the split blade housing; and a cam member rotatably supported by the cam plate, the cam member rotatable between a first closed position and a second, open position and including a base having a first can pin extending from the cam plate and received in the first cam slot of the first body portion of the mounting section of the split blade housing and a second cam pin extending from the cam plate and received in the second cam slot of the second body portion of the mounting section of the split blade housing, in the first, closed position of the cam member, the first cam pin is positioned nearer the first end portion of the first cam slot, the second cam pin is positioned nearer the first end portion of the second cam slot and the split distance between the first and second circumferential ends of the inner wall being a first value, in the second, open position of the cam member, the first cam pin is positioned nearer the second end portion of the first cam slot, the second cam pin is positioned nearer the second end portion of the second cam slot and the split distance between the first and second circumferential ends of the inner wall being a second value, the second value being greater than the first value.

In another aspect, the present invention relates to a power operated rotary knife comprising: an annular rotary knife blade supported for rotation about a central axis of rotation; an elongated handle assembly extending along a longitudinal axis; a frame body coupled to a distal end of the elongated handle assembly, the frame body including a mounting pedestal; and a blade housing assembly coupled to the frame body and supporting the annular rotary knife blade for rotation about the central axis of rotation, the blade housing assembly including: a split blade housing including: an annular blade support section, an inner wall of the blade support section defining a blade bearing region; a mounting section extending from the blade support section; and a radially extending split extending through the mounting section and the inner wall of the blade support section and defining a split distance between first and second circumferential ends of the inner wall; the mounting section including a first body portion and a second body portion on opposite sides of the radially extending split, the first body portion including a first surface and an axially spaced apart second surface including a first cam slot extending transversely with respect to the radially extending split and having a first end portion and a spaced apart second end portion; and a cam mechanism including: a cam plate bridging the first and second body portions of the mounting section of the split blade housing; and a cam member rotatably supported by the cam plate, the cam member rotatable between a first, closed position and a second, open position and including a base having a first cam pin extending from a first surface of the base and received in the first cam slot of the first body portion of the mounting section of the split blade housing, in the first, closed position of the cam member, the first cam pin is positioned nearer the first end portion of the first cam slot and the split distance between the first and second circumferential ends of the inner wall being a first value, in the second, open position of the cam member, the first cam pin is positioned nearer the second end portion of the first cam slot and the split distance between the first and second circumferential ends of the inner wall being a second value, the second value being greater than the first value frame body, the cam mechanism securing the mounting section of the split blade housing to the mounting pedestal of the frame body.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

DETAILED DESCRIPTION

The descriptions and disclosures, including drawings, relating to hand held, power operated rotary knives 100, 1000, 2000 and 3000, of the first, second, third and fourth exemplary embodiments, and components and assemblies thereof, and the rotary knife blade—blade housing assembly 4500 of the fifth exemplary embodiment, and components thereof, as disclosed in parent U.S. application Ser. No. 15/374,207 (hereinafter "the '207 application"), filed Dec. 9, 2016 and entitled POWER OPERATED ROTARY KNIFE, assigned to the assignee of the present application, are hereby fully incorporated herein by reference in their respective entireties by reference. For brevity, the descriptions of the power operated rotary knives will not be repeated herein.

Sixth Embodiment—Power Operated Rotary Knife 6000

A sixth exemplary embodiment of a power operated rotary knife of the present disclosure is shown generally at 6000 in FIGS. 1-9. The power operated rotary knife 6000 extends between a distal or forward end 6001 and a proximal or rearward end 6002 of the power operated rotary knife 6000. The power operated rotary knife 6000 includes an elongated handle assembly 6110, a head assembly, which is releasably secured to a front or distal end 6112 of the handle assembly 6110, and a drive mechanism 6600, including a gear train 6604. The handle assembly 6110 includes a central throughbore 6115 that extends along a central longitudinal axis LA of the handle assembly 6110. The head assembly 6200 extends from the handle assembly 6110 along the central longitudinal axis LA in a forward or distal direction FW. The throughbore 6115 of the handle assembly 6110 receives a distal portion of a flexible drive shaft assembly (similar to the flexible drive shaft assembly 700 of the first exemplary embodiment) which rotates the drive mechanism 6600, as described in the first exemplary embodiment of the '207 application. As used herein, the forward direction FW will be a direction extending generally along or parallel to the handle assembly longitudinal axis toward the distal end 6001 of the power operated rotary knife 6000 and a rearward direction RW will be a direction extending generally along or parallel to the handle assembly longitudinal axis toward the proximal end 6002 of the power operated rotary knife 6000.

Figure 8:
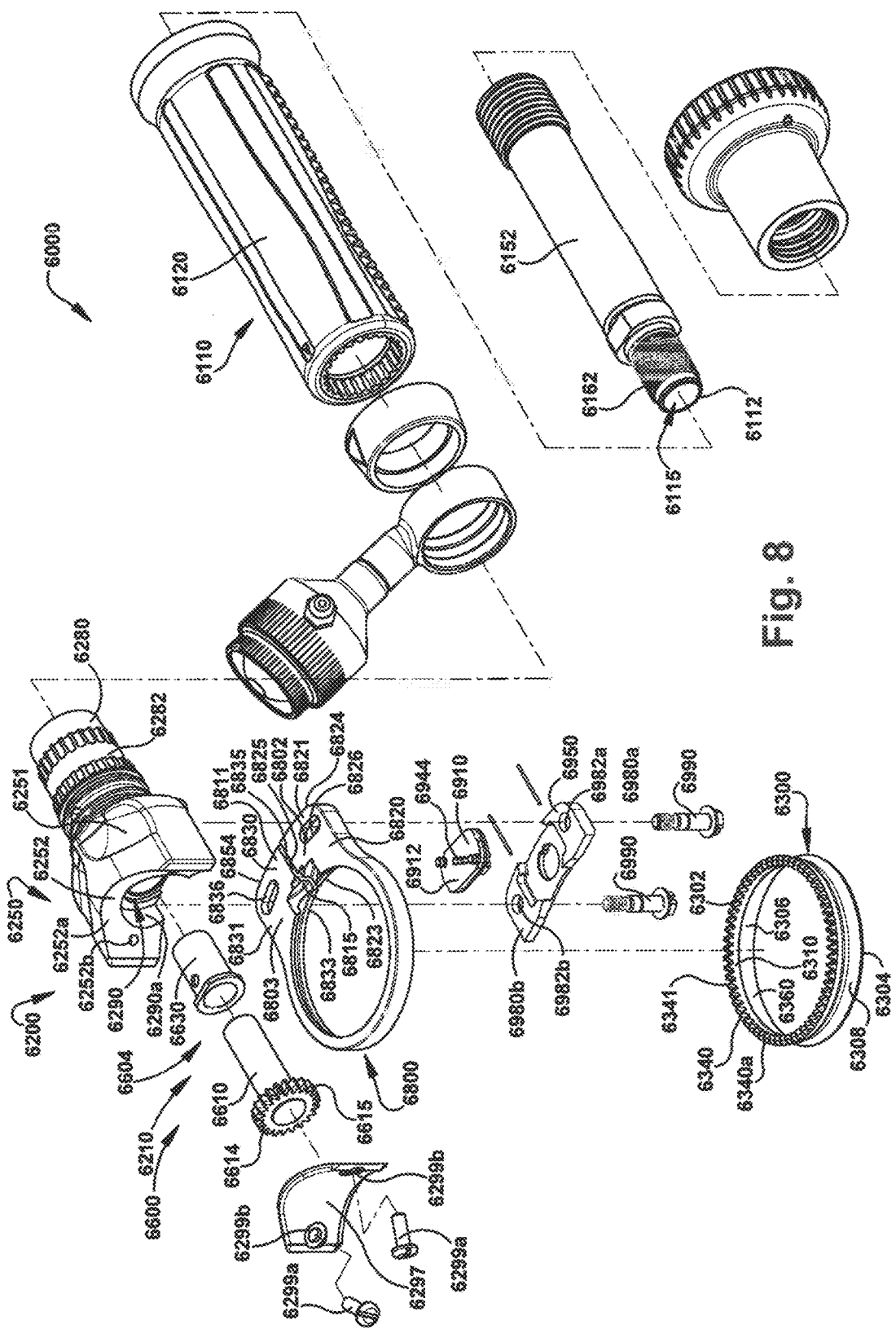
FIG. 8 is a schematic exploded, top, front perspective view of the power operated rotary knife of FIG. 1.
Figure 9:
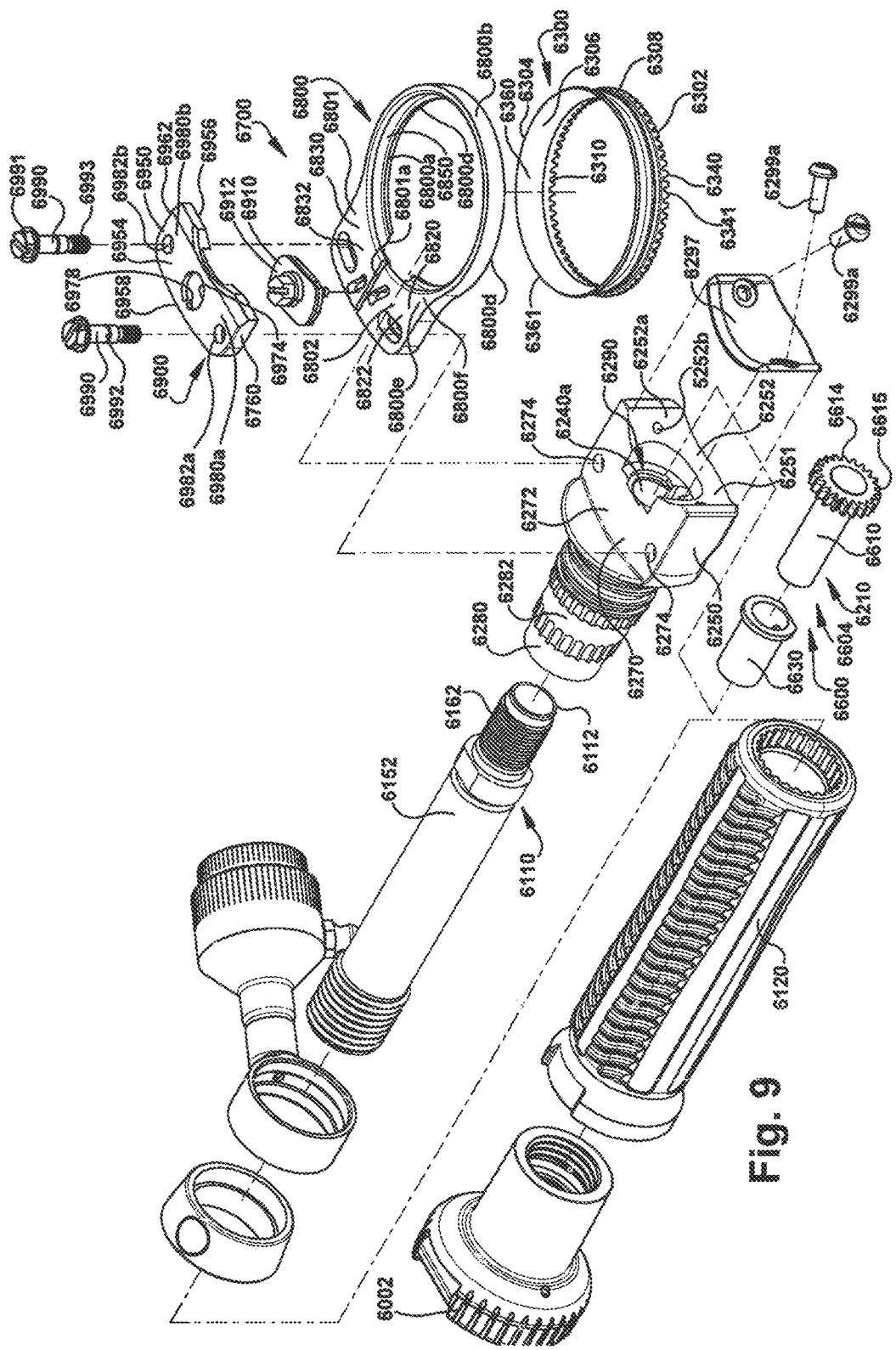
FIG. 9 is a schematic exploded, bottom, front perspective view of the power operated rotary knife of FIG. 1.

As best seen in FIGS. 8 and 9, the head assembly 6200 includes a frame body 6250 including a forward portion 6251 and a rearward portion 6280. The rearward portion 6280 of the frame body 6250 includes an annular boss 6282 that defines a mounting structure that receives and engages the front end 6112 of the handle assembly 6110 to secure the head assembly 6200 to the handle assembly 6110. The head assembly 6200 further includes an annular rotary knife blade 6300, substantially similar to the annular rotary knife blade 2300 of the power operated rotary knife 2000 of the third exemplary embodiment of the '207 application, and a blade housing assembly 6700 including a split blade housing 6800 which supports the annular rotary knife blade 6000 for rotation about a central axis of rotation R. The annular rotary knife blade 6300 includes an upper body 6310 and a lower blade section 6360 extending from the body 6310. The annular rotary knife blade 6300 is rotatably driven by the drive mechanism 6000, as previously described. The forward portion 6251 of the frame body 6250 supports the drive mechanism 6600 and positions a gear head 6614 of a pinion gear 6610 of the gear train 6604 of the drive mechanism 6600 to interface with a driven gear 6340 of the body 6310 of the rotary knife blade 6300 to thereby rotate the blade 6300 about its central axis of rotation R.

Figure 1:
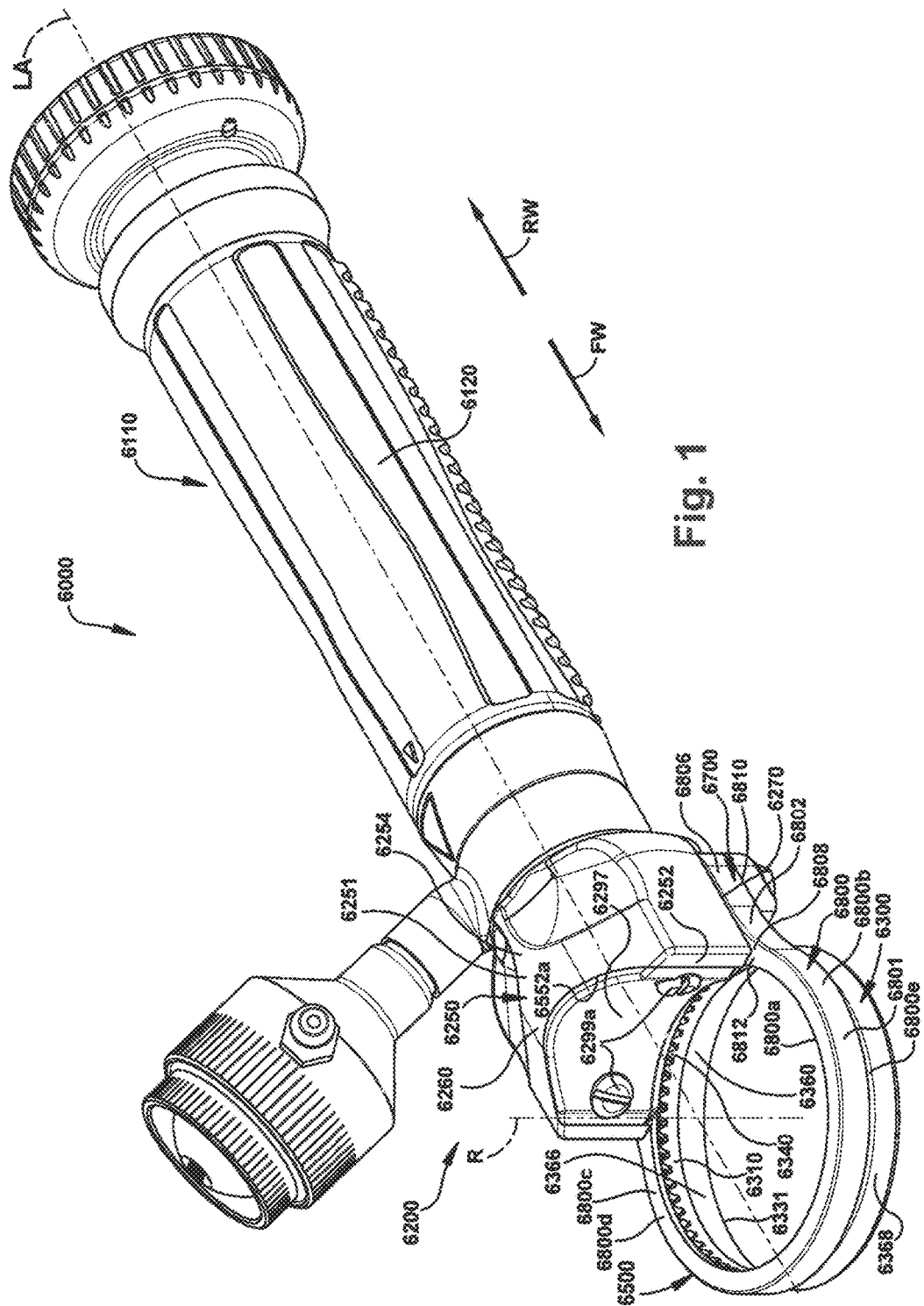
FIG. 1 is a schematic top, front perspective section view of a sixth exemplary embodiment of a power operated rotary knife of the present disclosure, including a head assembly, a handle assembly and a drive mechanism, the head assembly including a frame body, an annular rotary knife blade and a blade housing assembly supporting the annular rotary knife blade for rotation, the blade housing assembly including an annular split ring blade housing and a cam mechanism coupled to the blade housing to selectively move the blade housing between a first, blade supporting position and a second, blade changing position.
Figure 2:
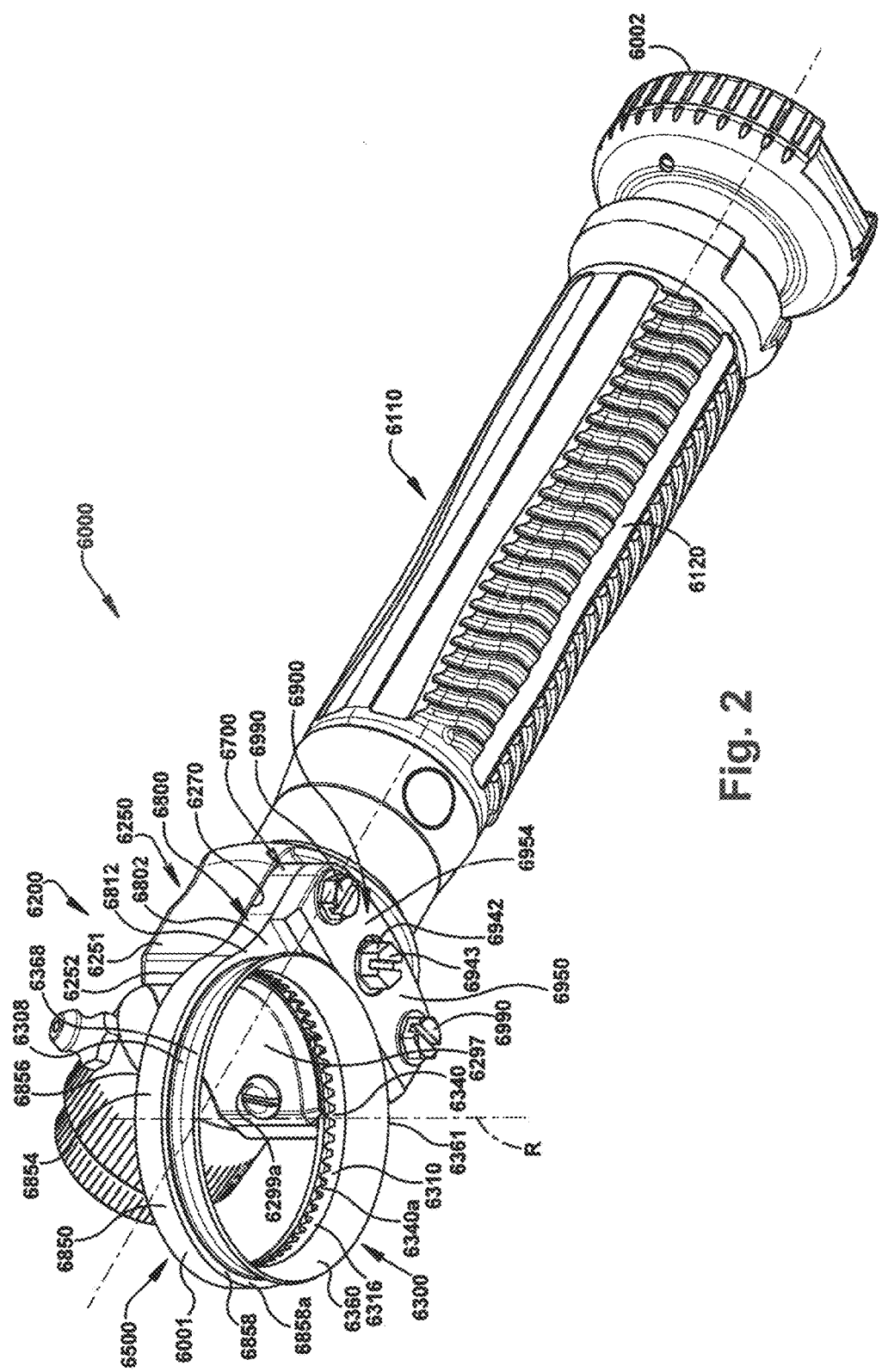
FIG. 2 is a schematic bottom, front perspective view of the power operated rotary knife of FIG. 1.
Figure 3:
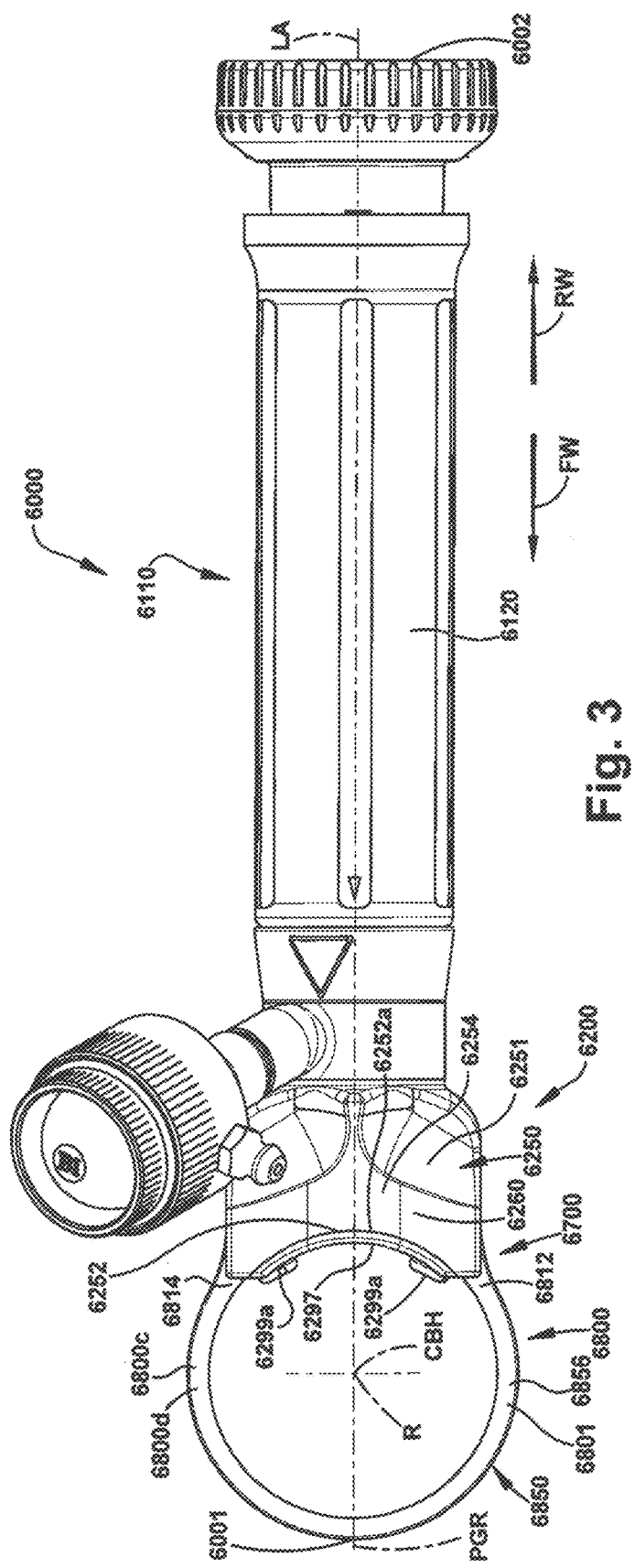
FIG. 3 is a schematic top plan view of the power operated rotary knife of FIG. 1.
Figure 4:
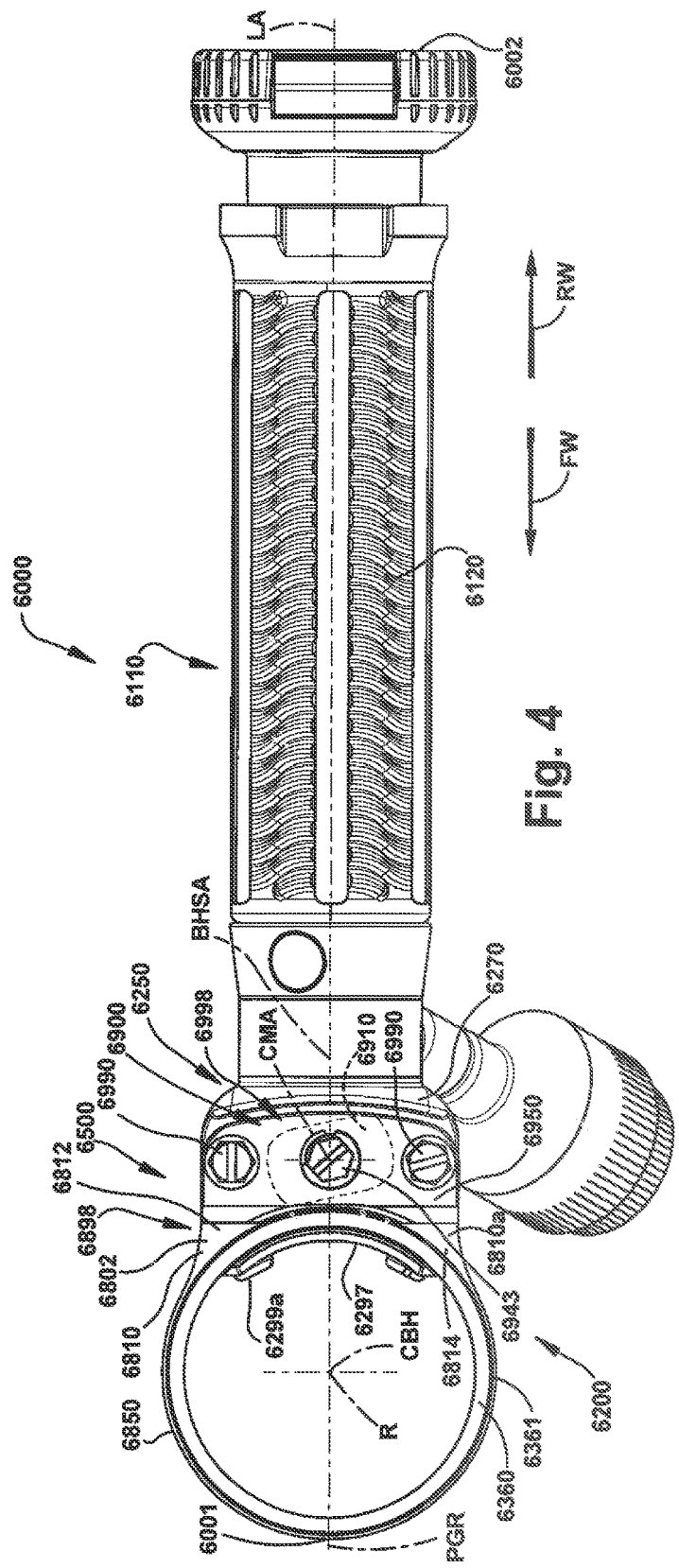
FIG. 4 is a schematic bottom plan view of the power operated rotary knife of FIG. 1.
Figure 5:
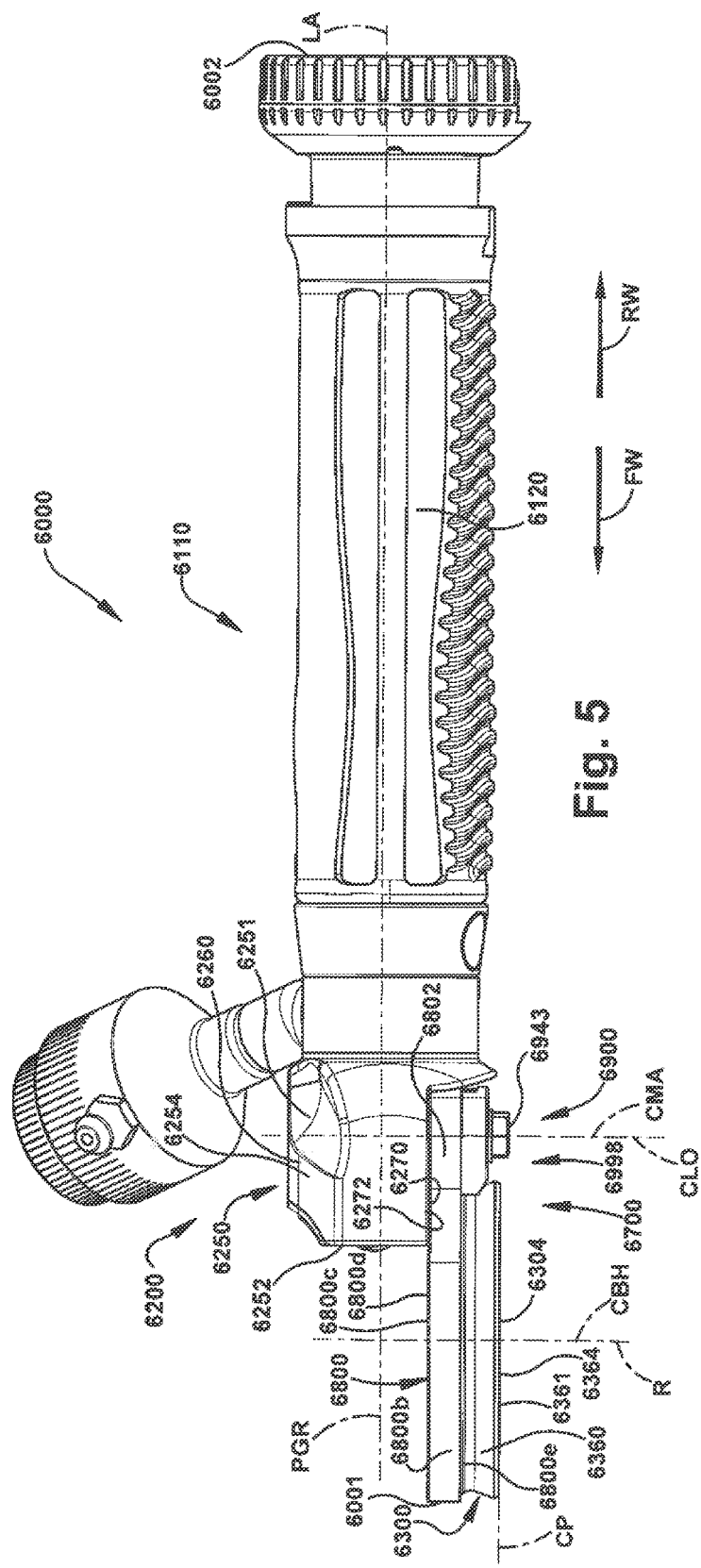
FIG. 5 is a schematic side elevation view of the power operated rotary knife of FIG. 1.
Figure 6:
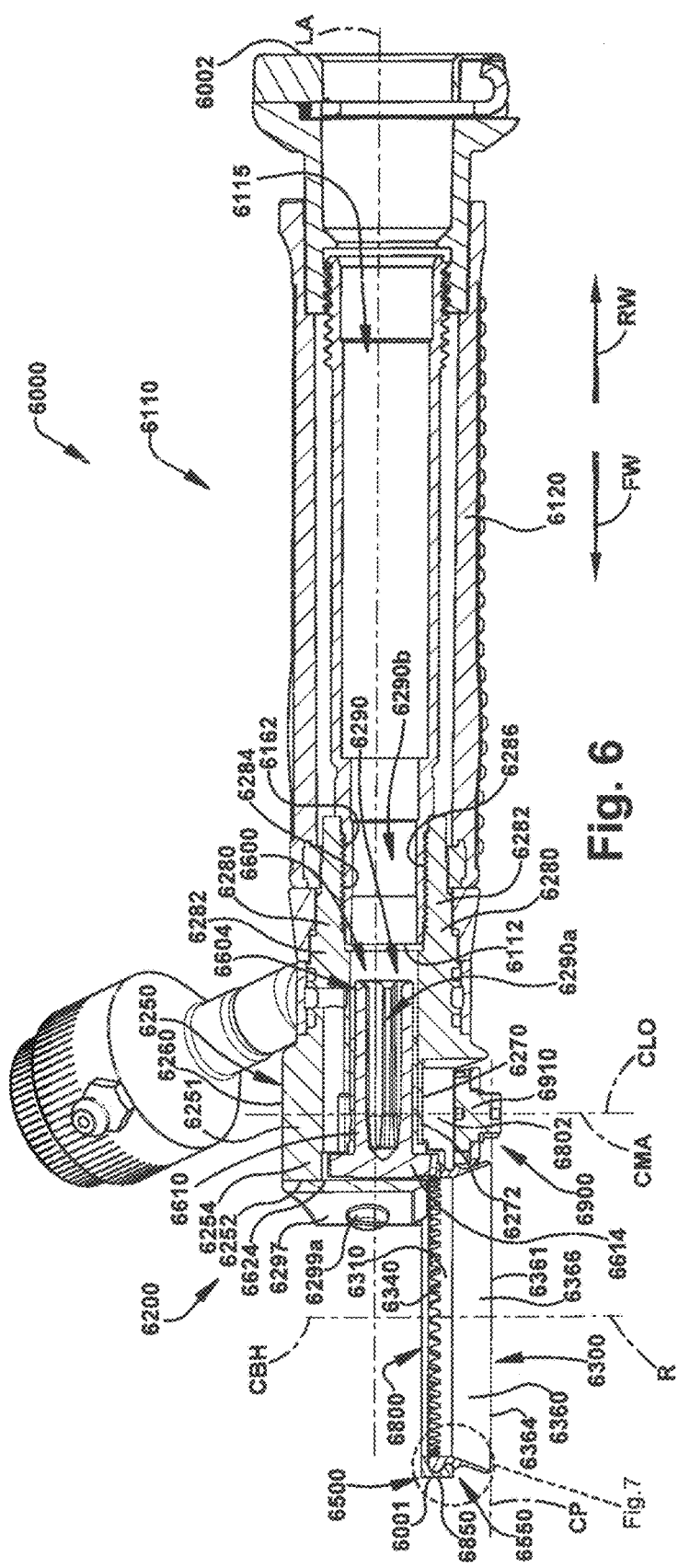
FIG. 6 is a schematic vertical section view taken along a longitudinal axis of the handle assembly of the power operated rotary knife of FIG. 1.
Figure 7:
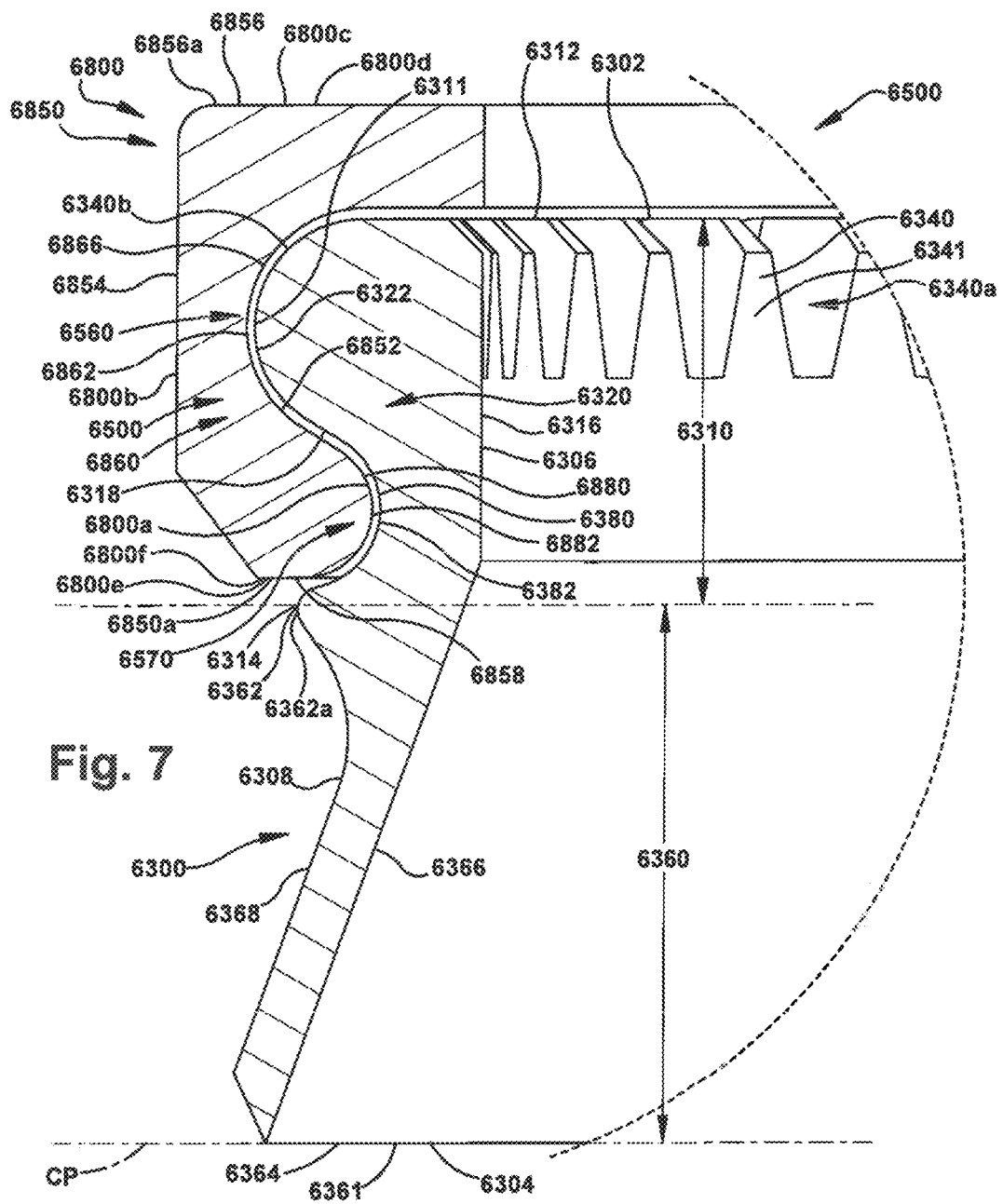
FIG. 7 is a schematic enlarged vertical section view of the power operated rotary knife of FIG. 1 which is within a circle labeled FIG. 7 in FIG. 6.

As best seen in FIGS. 6 and 7, an assembled blade—blade housing combination 6500 includes the annular rotary knife blade 6300 and the split blade housing 6800 supporting the rotary knife blade 6300 for rotation about the annular rotary knife blade's central axis of rotation R. The assembled blade—blade housing combination 6500 includes a blade—blade housing bearing structure 6550, similar to the blade—blade housing bearing structure 2550 of the assembled blade—blade housing combination 2500 of the third exemplary embodiment of the '207 application. More specifically, the blade—blade housing bearing structure 6550 includes two axially spaced apart bearing structures, namely, a first blade—blade housing bearing structure 6560 and a second blade—blade housing bearing structure 6570.

Various components and assemblies of the power operated rotary knife 6000 are substantially similar in structure and/or function to corresponding components and assemblies of the power operated rotary knife 2000 of the third exemplary embodiment of the '207 application. In the interest of brevity, components and assemblies of the power operated rotary knife 6000 that are similar to the corresponding components and assemblies of the power operated rotary knife 2000 of the third exemplary embodiment in structure and/or function will not be fully described herein. Instead, reference is made to the description of such components and assemblies set forth above in connection with the power operated rotary knife 2000 and/or the power operated rotary knife 100 of the first exemplary embodiment and/or the power operated rotary knife 1000 of the second exemplary embodiment and/or the power operated rotary knife 3000 of the fourth exemplary embodiment and/or the blade—blade housing combination 4500 of the fifth exemplary embodiment, as set forth in the '207 application. Materials/fabrication of components and assemblies of the power operated rotary knife 6000 are similar to materials/fabrication of corresponding components and assemblies of the power operated rotary knives 100, 1000, 2000, 3000 and the blade—blade housing combination 4500, as described in the '207 application. Such descriptions of components and assemblies of the power operated rotary knives 100, 1000, 2000, 3000 and the blade—blade housing combination 4500 are hereby incorporated by reference from the '207 application in the following description of the power operated rotary knife 6000 of the sixth exemplary embodiment. Identification of axes, lines, planes and directions for the power operated rotary knife 6000, as set forth herein, will be the same as used for the description of the power operated rotary knives 100, 1000, 2000, 3000 in the '207 application.

Figure 23:
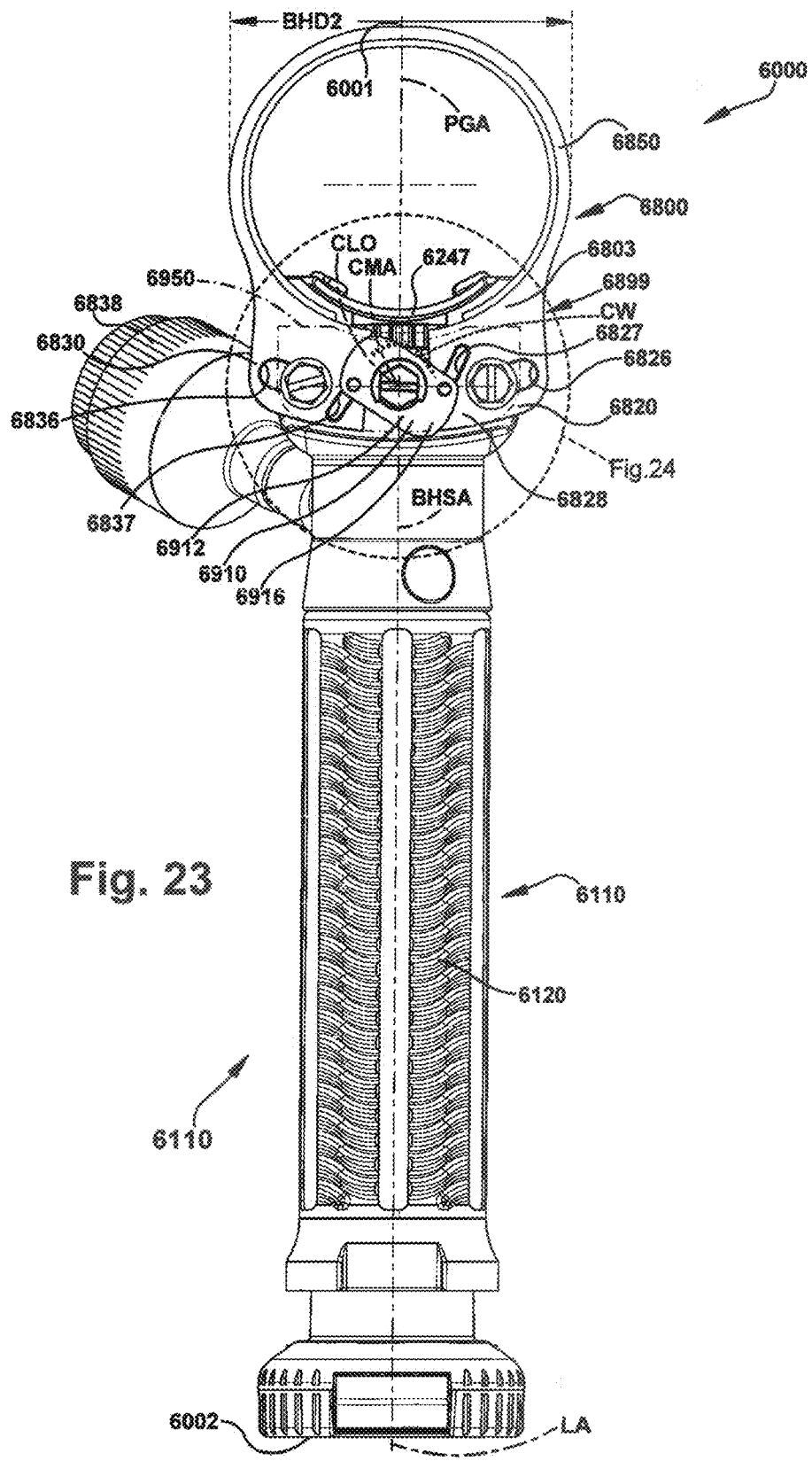
FIG. 23 is a schematic bottom plan view of the power operated rotary knife of FIG. 31 with the annular rotary knife blade removed and a cam plate of the cam mechanism of the blade housing assembly removed and with the cam mechanism in a second, open position and the annular split blade housing in the second, blade changing position.
Figure 24:
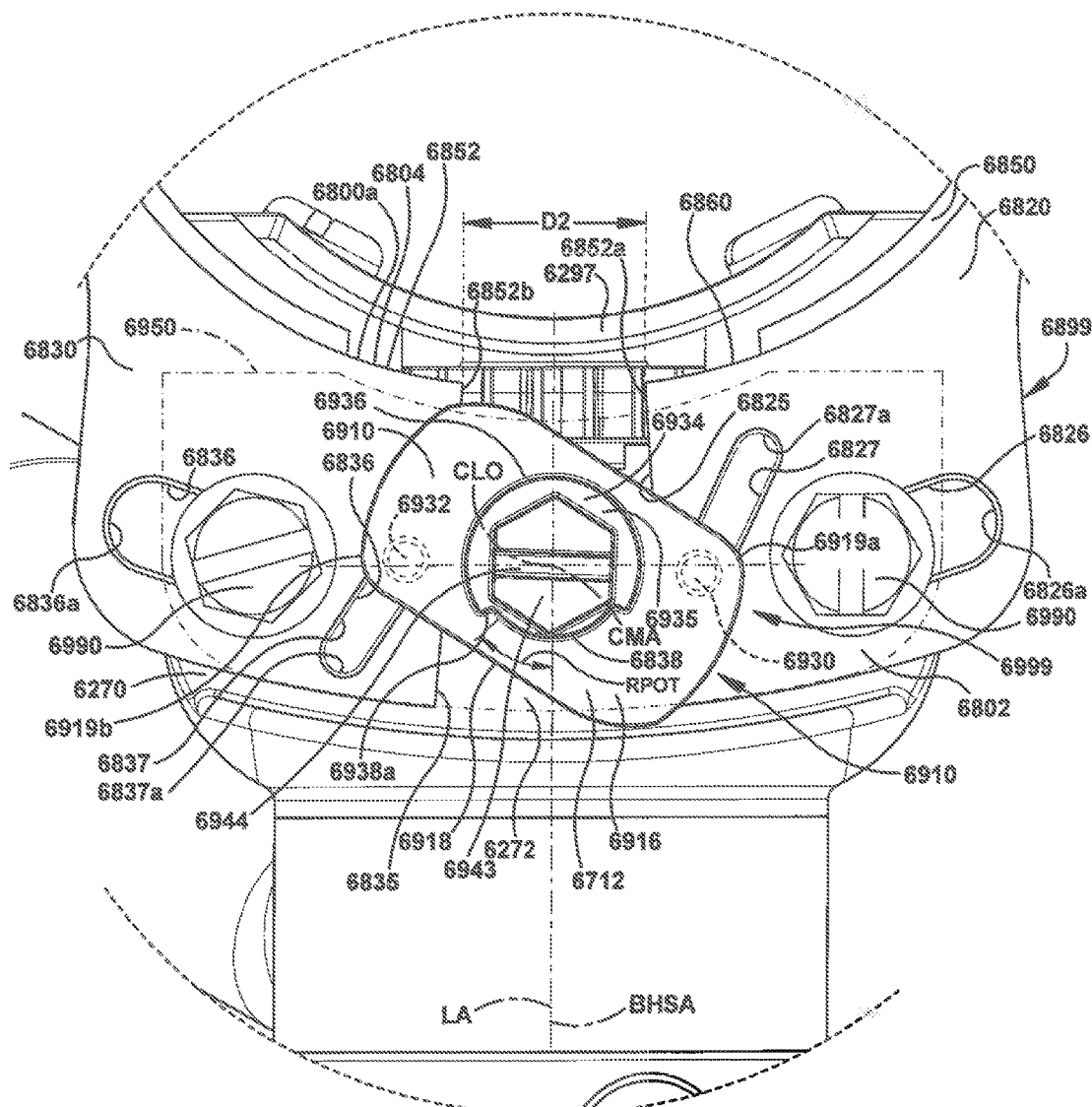
FIG. 24 is a schematic enlarged bottom plan view of a portion of the power operated rotary knife of FIG. 1 which is within a circle labeled FIG. 24 in FIG. 23 and with the cam mechanism in the second, open position and the annular split blade housing in the second, blade changing position.

Unique to the sixth exemplary embodiment of the power operated rotary knife 6000 is a blade housing assembly 6700 of the head assembly 6200 which functions to secure the rotary knife blade 6300 for rotation about the central axis of rotation R. As best seen in FIGS. 21-24, the blade housing assembly 6700 includes the split blade housing 6800 and a cam mechanism or cam assembly 6900 affixed to the split blade housing 6800 which, in a first, closed, locked or home position 6998 of the cam mechanism 6900, secures the blade housing 6800 in a first, blade supporting position 6898, characterized by a first, unexpanded or blade supporting blade housing diameter BHD1 (depicted schematically in FIG. 21), and, in a second, open, unlocked or expanded position 6999 of the cam mechanism 6900, secures the blade housing 6800 in a second, blade changing position 6899, characterized by a second, expanded blade housing diameter BHD2 (FIG. 23). The blade housing 6800 includes an annular blade support section 6850 which supports the rotary knife blade 6300 for rotation and a mounting section 6802, which may be considered as a tongue or projection extending radially outwardly and in a generally rearward direction RW from the annular blade support section 6850.

The first and second blade housing diameters BHD1, BHD2 are measured with respect to the outer diameter of the annular blade support section 6850 in a direction. generally orthogonal to the handle assembly longitudinal axis LA. It is to be understood, of course, that the second blade housing diameter BHD2 is larger than the first blade housing diameter BHD1 to facilitate removal of the annular rotary knife blade 6300 from the split blade housing 6800 when the blade housing 6800 is in the second, blade changing position 6899. It being further understood that the bearing interface between a blade bearing region 6320 of the annular rotary knife blade 6300 and a blade housing bearing region 6860 of the blade support section 6850 of the blade housing 6800 together comprising the blade—blade housing structure 6550 of the power operated rotary knife 6000 support the blade 6300 for rotation about its central axis of rotation R. When the blade housing diameter moves from the first, unexpanded blade housing diameter BHD1 to the second, expanded blade housing diameter BHD2, a diameter of a bearing region 6860 of the blade support section 6850 of the blade housing 6800 expands proportionately with the outer diameter of the blade housing 6800 as the diameter changes from BHD1 to BHD2, thus, the diameter of the bearing region 6860 of the blade support section 6850 of the blade housing 6800 expands sufficiently to allow removal of the annular rotary knife blade 6300 from the blade support section 6850 of the blade housing 6800. Stated another way, since the diameter of the bearing region 6860 of the blade support region 6850 of the blade housing 6800 is directly proportional to the outer diameters BHD1, BHD2 of the blade support section 6850, the blade housing outer diameters BHD1, BHD2 may be used as a convenient surrogate for the respective first, unexpanded diameter and second, expanded diameter of the blade housing bearing region 6860 as the blade housing 6800 moves from the first, blade supporting position 6898 to the second, open or expanded position 6899. Thus, for the specific parameters of the bearing interface or structure 6550 between the respective diameters of blade and blade housing bearing regions 6320, 6860, the second blade housing diameter BHD2 is sized to be a Magnitude that is sufficiently large such that the annular rotary knife blade 6300 drops downwardly out of or is easily removed from the blade housing blade support section 6850 when the blade housing 6800 has been moved to the second, blade changing position 6899.

Advantageously, the cam mechanism 6900 functions both to: a) secure the assembled blade—blade housing combination 6500 to the frame body 6250; and b) as desired, allows an operator or maintenance person to selectively change the diameter of the blade support section 6850 of the blade housing 6800 between the first, unexpanded blade housing diameter BHD1 (for purposes of supporting the rotary knife blade 6300 for rotation about the central axis of rotation during use of the power operated rotary knife 6000) and the second, expanded blade housing diameter BHD2 (for purposes of removing the rotary knife blade 6300 from the blade housing 6800 for purposes of sharpening, blade changing, cleaning and/or maintenance of the power operated rotary knife 6000). That is, in the first, closed position 6998 of the cam mechanism 6900, the cam mechanism 6900 holds or secures the split blade housing 6800 in the first, blade supporting position 6898 wherein the annular rotary knife blade 6300 is supported for rotation about its central axis of rotation R, and, in the second closed position 6999 of the cam mechanism 6900, the cam mechanism 6900 secures the split ring blade housing 6800 in the second, blade changing position 6899 wherein the diameter of the blade support section 6850 is increased from BHD1 to BHD2 to allow for removal of the annular rotary knife blade 6300 from the split ring blade housing 6800 to allow for sharpening or replacement of the rotary knife blade 6300 and/or cleaning of the components of the head assembly 6200 of the power operated rotary knife 6000. The blade housing diameter in the first, blade supporting position 6898 is blade housing diameter BHD1 corresponding to the first, closed position 6998 of the cam mechanism 6900, is blade housing diameter BHD1 and the blade housing inner diameter in the second, blade changing position 6899, corresponding to the second, open position 6998 of the cam mechanism 6900, is blade housing diameter BHD2.

As can best be seen in FIGS. 8-11, the split blade housing 6800 comprises a split ring 6801 and includes a radial split 6801a extending through a diameter of the blade housing 6800 in the region of the blade housing mounting section 6802 to allow for expansion of a circumference of the annular blade support section 6850 for purposes of removing the annular rotary knife blade 6300 from the annular blade support section 6850 and inserting a new or resharpened annular rotary knife blade 6300 into the annular blade support section 6850. With respect to the mounting section 6802, the radially extending split 6801a bisects a planar central region 6811 of the mounting section 6802 defining a first body section or portion 6820 on one side of the split 6801a and a second body section or portion 6830 on an opposite side of the split 6801a. Advantageously, as can best be seen in FIGS. 2, 4 and 21-24, the cam mechanism 6900 is mounted to the central region 6811 of the mounting section 6802 and bridges the first and second body portions 6820, 6830. The radially extending split 6801a defines a radially extending split axis BHSA of the blade housing mounting section 6802. The blade housing split axis BHSA is substantially orthogonal to and intersects a center line or central axis CBH of the blade housing 6800. The blade housing center line CBH substantially coincident with the central axis of rotation R of the rotary knife blade 6300.

Figure 10:
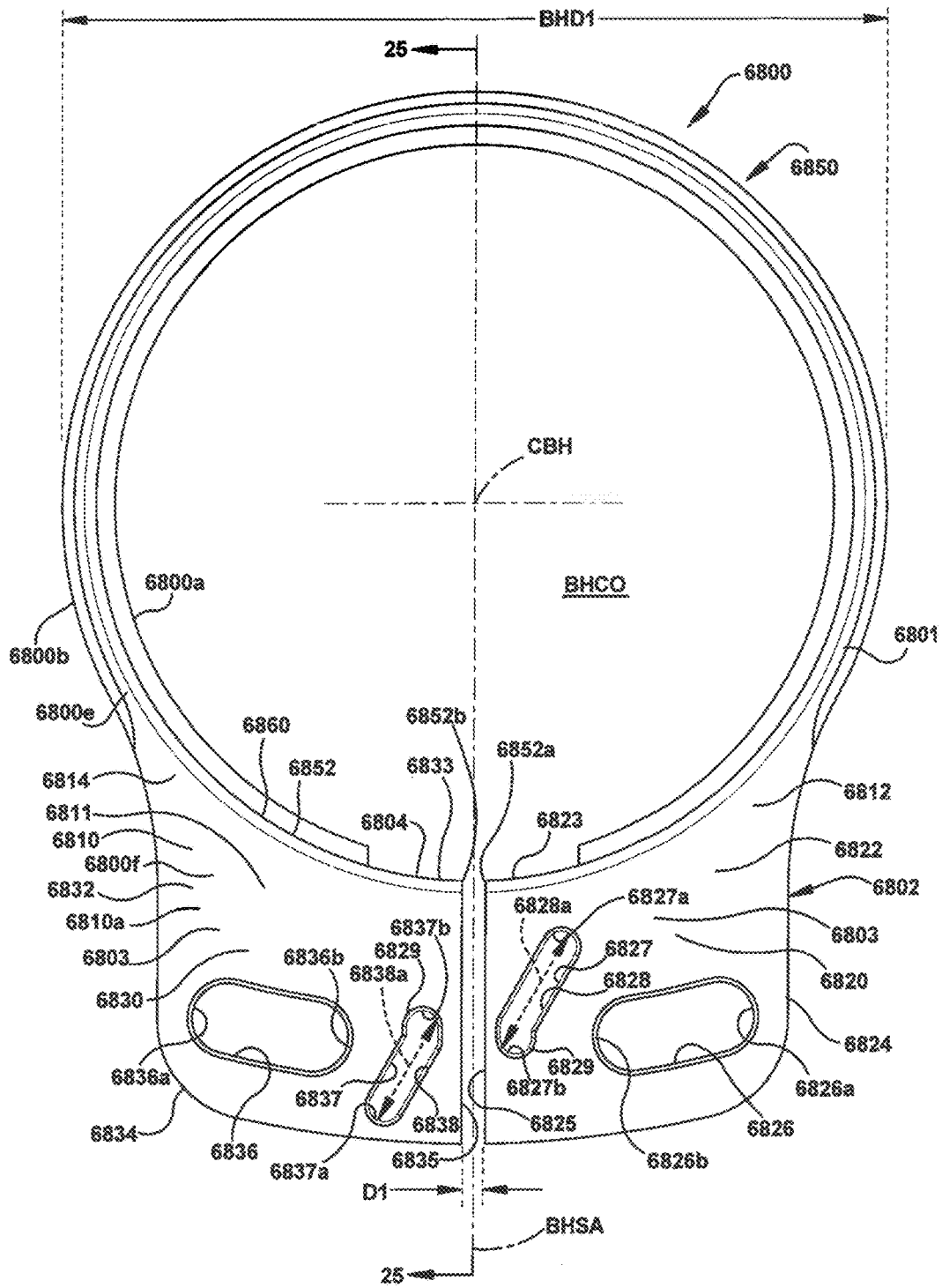
FIG. 10 is a schematic bottom plan view of the annular split ring blade housing of the power operated rotary knife of FIG. 1.
Figure 11:
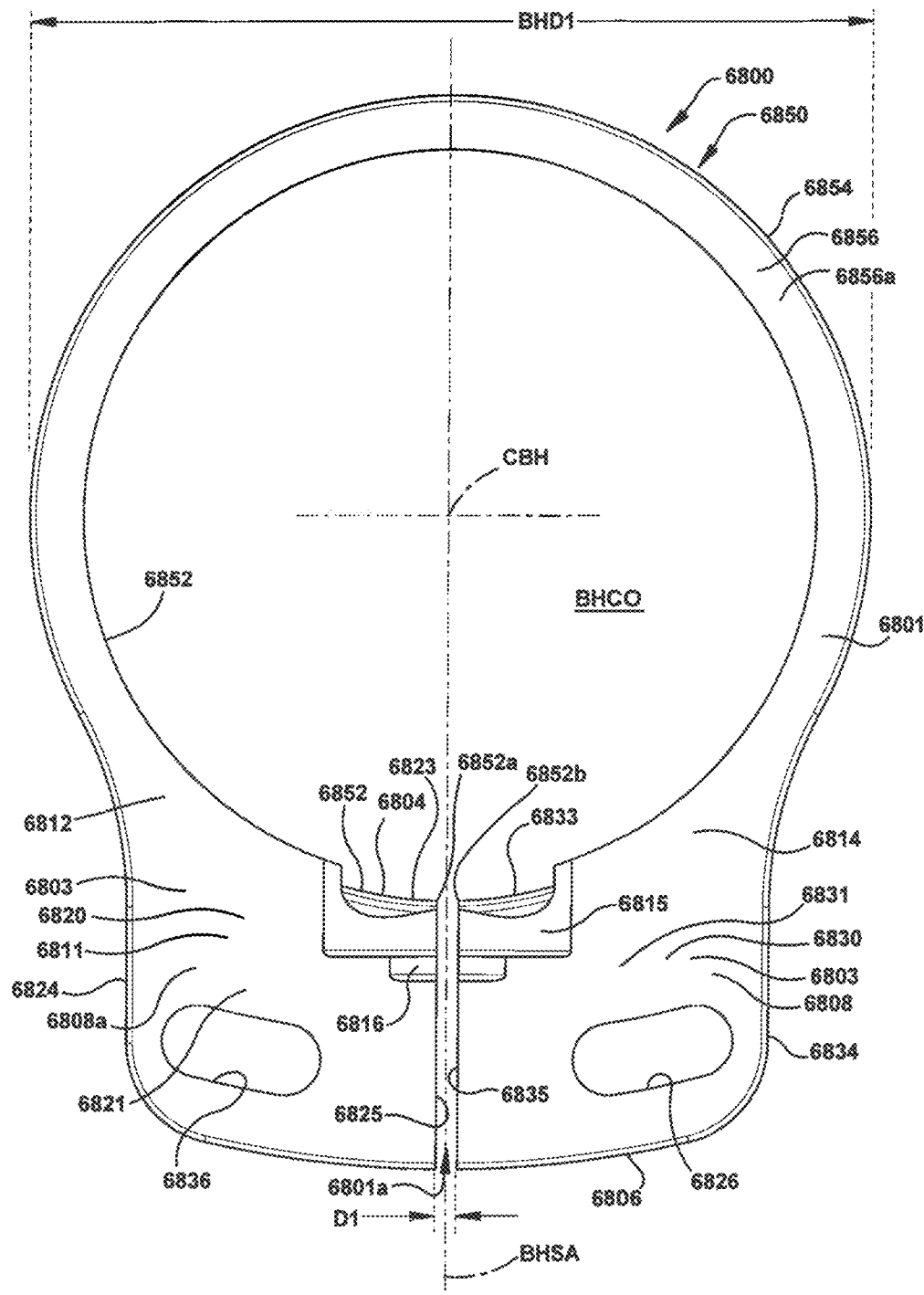
FIG. 11 is a schematic top plan view of the annular split ring blade housing of FIG. 10.
Figure 12:
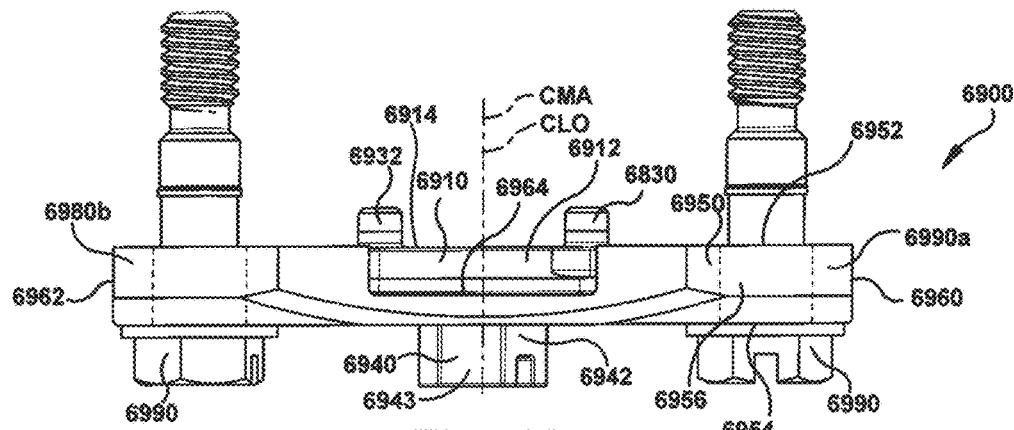
FIG. 12 is a schematic front elevation view of the cam mechanism of the power operated rotary knife of FIG. 1.
Figure 13:
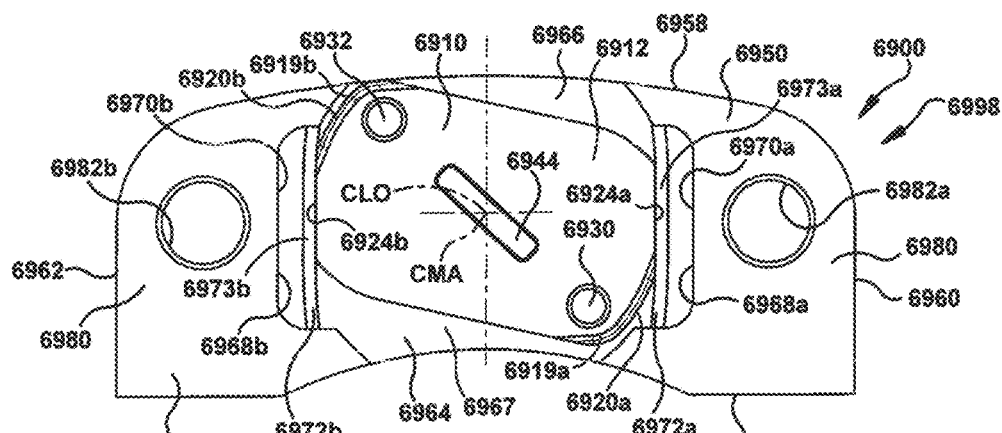
FIG. 13 is a schematic top plan view of the cam mechanism of FIG. 12.
Figure 14:
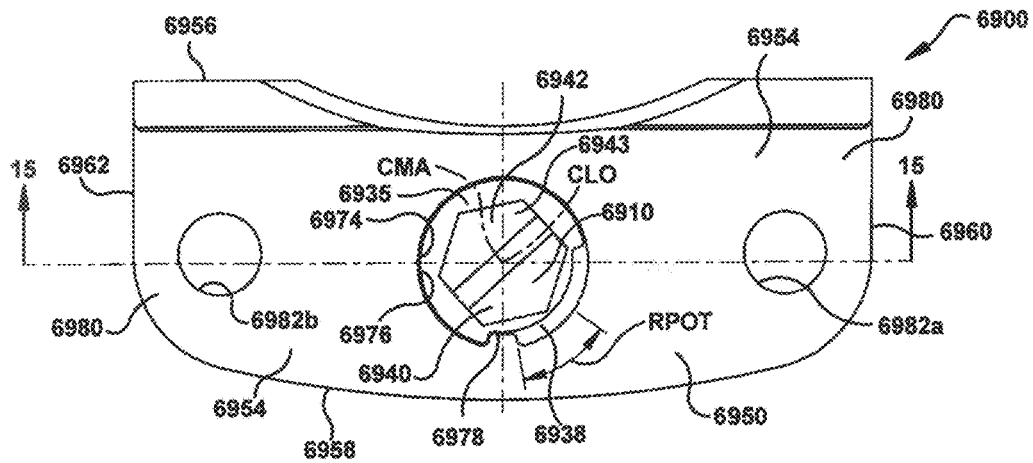
FIG. 14 is a schematic bottom plan view of the cam mechanism of FIG. 12.
Figure 15:
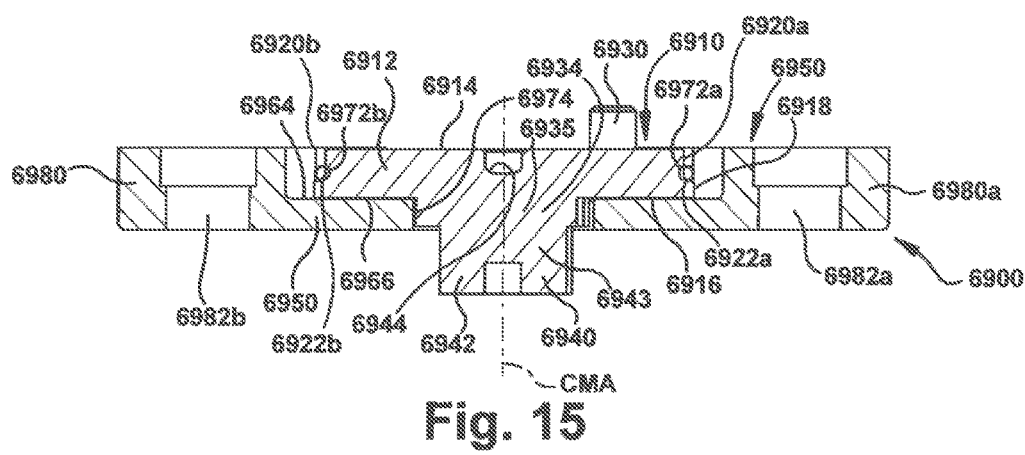
FIG. 15 is a schematic vertical section view of the cam mechanism of FIG. 12 as seen from a plane indicated by the line 15-15 in FIG. 14.
Figure 16:
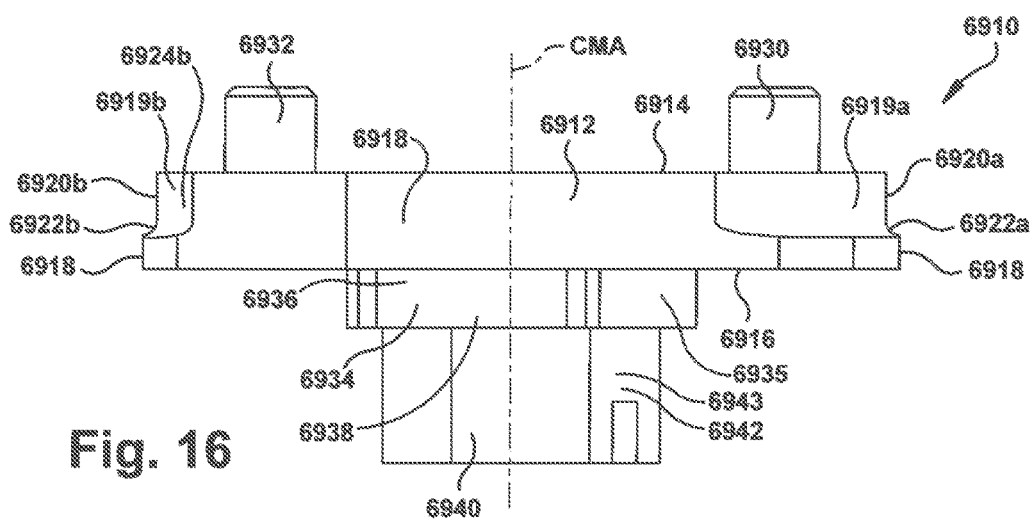
FIG. 16 is a schematic front elevation view of a cam member of the cam mechanism of FIG. 12.
Figure 25:
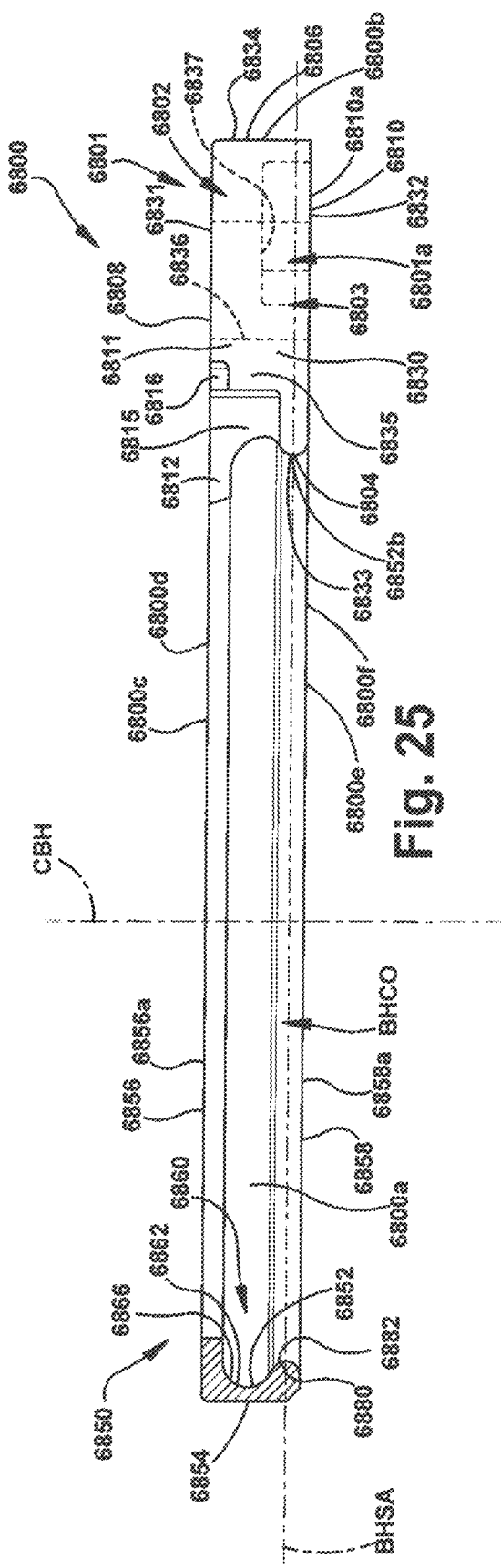
FIG. 25 is a schematic section view the annular split ring blade housing of FIG. 10 as seen from a plane indicated by the line 25-25 in FIG. 10.

As best seen in FIGS. 10, 11 and 25, the blade housing split 6801a extends through both the annular blade support section 6850 and the mounting section 6802 extending from the blade support section 6850. In reality, the blade housing split axis BHSA is a plane (as opposed to a line) that extends between opposing faces 6825, 6835 of the first and second body portions 6820, 6830 of the blade housing mounting section 6802. However, for sake of simplicity, the blade housing split plane will be referred to the blade housing split axis BHSA. The cam mechanism 6900 of the blade housing assembly 6700 includes a cam member 6910 rotatably supported by a cam plate 6950. The cam member 6910 rotates about an axis of rotation CMA that is offset from, but substantially parallel to the central axis of rotation R of the rotary knife blade 6300. The cam member axis of rotation CMA is substantially orthogonal to and intersects the longitudinal axis LA of the handle assembly 6110 and is substantially orthogonal to and intersects the split axis BHSA defined by the blade housing split 6801a. Changing or rotating the cam mechanism 6900 from the first, closed position 6998 (corresponding to the blade supporting position 6898 of the blade housing 6800) to the second, open position 6999 (corresponding to the blade changing position 6899 of the blade housing 6800) increases a width of the split 6801a, that is, the split width or split distance of a gap between opposing faces 6825, 6835 of the first and second body portions 6820, 6840. In the first closed position 6998 of the cam mechanism 6900 (corresponding to the first, blade supporting position 6898 of the blade housing 6800), the gap or split distance between the opposing faces 6825, 6835 is a first blade housing split width or split distance D1 and in the second open position 6999 of the cam mechanism 6900 (corresponding to the second, blade changing position 6899 of the blade housing 6800), the gap or split distance between the opposing faces 6830, 6850 is a second blade housing split width or split distance D2.

The blade housing split distances D1, D2 are measured orthogonally to a radial direction of the split 6801a, that is, orthogonally to the blade housing split axis BHSA and parallel to a cutting plane CP of the rotary knife blade 6300 at an inner wall 6852 of the blade support section 6850 of the blade housing 6800. The blade housing split distances D1, D2 for a particular blade housing, of course, will vary depending on the specific characteristics of the cam mechanism 6900 and the position and length of the corresponding cam slots 6827, 6837 of the blade housing mounting section 6802. Specifically, as can be seen in FIGS. 10-11, 22 and 24, the blade housing split distances D1, D2 are measured between circumferentially spaced apart ends 6852a, 6852b of the inner wall 6852 of the blade support section 6850 of the blade housing 6800 adjacent the split 6801a. In one exemplary embodiment, the blade housing split distance D1 corresponding to the first, blade supporting position 6898 of the blade housing 6800 is approximately 0.06 in., while the blade housing split distance D2 corresponding to the second, blade changing position 6899 of the blade housing 6800 is approximately 0.36 in. In one exemplary embodiment, the blade housing outer diameter BHD1 corresponding to the first, blade supporting position 6898 of the blade housing 6800 is approximately 1.85 in., while the blade housing outer diameter BHD2 corresponding to the second, blade changing position 6899 of the blade housing is approximately 1.95 in. It being understood, of course, that the dimensions of the split blade housing 6800 and the cam mechanism 6900 and the required blade housing split distances D1, D2 and blade housing diameters BHD1, BHD2 will necessarily change based on a number of parameters of the power operated rotary knife including: a) the diameter or size of the rotary knife blade to be supported by the blade housing; b) the dimensions and configuration of the blade—blade housing bearing structure; and c) the specific style, configuration, dimensions, characteristics and parameters of the rotary knife blade and/or the blade housing and/or other components of the power operated rotary knife 6000. The dimensions set forth herein are merely illustrative or representative of one exemplary embodiment of the blade—blade housing combination 6500 and the power operated rotary knife 6000.

As can best be seen in FIG. 7, due to the fact that the assembled blade—blade housing combination 6500 includes the double axial blade—blade housing bearing structure 6550 having two axially spaced apart bearing structures, namely, a first blade—blade housing bearing structure 6560, and a second blade—blade housing bearing structure 6570, the extent of radial overlap between the blade bearing region 6320 and the blade housing bearing region 6860 is defined by an overlap of a portion of an outer wall 6318 of the body of annular rotary knife blade 6300 and a portion of the inner wall 6852 of the blade support section 6850 of the blade housing 6800. Advantageously, the cam mechanism 6900 is designed to provide for sufficient difference or delta between the blade housing split distances D1, D2 and between the blade housing diameters BHD1, BHD2 to allow for removal of the rotary knife blade 6300 from the blade housing 6800 when the cam mechanism 6900 is in the second, open position 6999. The cam mechanism 6900 advantageously provides for: a) a simple, durable and repeatable mechanical assembly allowing an operator or maintenance person to increase in the diameter of the blade support section 6850 to a predetermined, desired blade housing diameter BHD2 corresponding to the blade housing blade changing configuration 6899 that is sufficiently large for blade removal purposes; and, b) equally important, a simple, durable and repeatable mechanical assembly allowing the operator or maintenance person to return in the diameter of the blade support section 6850 back to a predetermined, desired blade housing diameter BHD1 corresponding to the blade housing blade support configuration 6898 having a proper, desired operating or running clearance for the rotary knife blade 6300, without the need for further operator or maintenance person adjustment of the blade housing diameter. That is, after the cam mechanism 6900 is actuated to move or rotate the cam member 6950 of the cam mechanism 6900 to the first, closed position 6999, the power operated rotary knife 6000 is ready for use by the operator without further adjustment to the blade housing 6880 to change the operating or running clearance. The cam mechanism 6900 of the blade housing assembly 6700 is advantageous compared to the conventional technique of blade removal in a power operated rotary knife taught, for example, in U.S. Pat. No. 6,978,548 to Whited et al. The '548 patent discloses a blade housing structure including an expansion slot formed in the outer periphery of the blade housing. Upon loosening one of the two clamping fasteners securing the assembled blade—blade housing combination to a frame body of the head assembly, a screwdriver may be inserted into the blade housing expansion slot and levered against the frame body to expand the blade housing diameter and thereby remove the rotary knife blade from the blade housing. The cam mechanism 6900 of the present disclosure eliminates the need for such an expansion slot and prying with a screwdriver, providing, instead, a more secure and consistent mechanism for blade housing expansion that provides for a reproducible and consistent expansion of the blade housing diameter between the first blade supporting position 6898 and the second blade changing position 6899 wherein the blade housing split distance D2 in the second blade changing position 6899 is sufficient to easily remove the rotary knife blade 6300 from the blade housing 6800.

Additionally, the assembled blade—blade housing combination 6500 includes the blade—blade housing bearing structure 6550 which has all of the advantages of extended useful life with respect to bearing and component wear, as described with respect to the blade—blade housing bearing structure 2550 of the assembled blade—blade housing combination 2500 of the power operated rotary knife 2000 of the third exemplary embodiment of the '207 application. Accordingly and advantageously, when a sharpened, cleaned or new annular rotary knife blade 6300 is installed in the blade housing 6800 and the cam mechanism 6900 is moved to its first closed position 6998, the diameter of the blade support section 6850 of the blade housing 6800 is set to a predetermined, consistent, desired diameter. Thus, because the diameter of the blade support section 6850 is set at a predetermined, desired diameter, a desired operating or running clearance between the blade 6300 and the blade housing 6800 in their respective bearing regions 6320, 6860 is correspondingly set and maintained by the cam mechanism 6900. Because of the advantageous wear characteristics of the respective bearing regions 6320, 6860 of the rotary knife blade 6300 and blade housing 6800 due to the two axially spaced apart bearing structures, namely, the a first blade—blade housing bearing structure 6560 and the second blade—blade housing bearing structure 6570, under proper cutting conditions and with proper maintenance, there may advantageously be no need for the operator of the power operated rotary knife 6000 to make any adjustment to the blade housing diameter to account for changes in the operating clearance of the assembled blade—blade housing combination 6500 during the course of a work shift. That is, due to the improved wear characteristics of the bearing structure 6560 of the assembled blade—blade housing combination 6500 of the power operated rotary knife 6000, the operator may not have to make any adjustments to operating clearance during a work shift to account for increasing looseness of the rotary blade within the blade housing as the contacting bearing surfaces wear over time during cutting or trimming operations. Such operator adjustment to the blade housing diameter to compensate for perceived looseness of the rotating blade within the blade housing (too much operating clearance) or perceived tightness of the rotating blade within the blade housing (too little operating clearance) are undesirable for a number of reasons. First, the time required for adjustment of the operating clearance is necessarily down time from cutting and trimming operations. Second, an inexperienced operator may perceive a need for adjustment and bounce between blade housing diameter positions where the operating clearance is less than optimal with the blade running too loosely within the blade housing causing vibration and excessive component wear, to blade housing diameter position where operating clearance is more than optimal with the blade being too tightly held within the blade housing causing excess heat generation and excessive component wear.

Thus, the cam mechanism 6900 of the present disclosure by advantageously providing for a single predetermined, consistent, desired operating or running clearance when the cam mechanism 6900 is set to the first, closed position 6998 may provide for a full shift operation of the power operated rotary knife 6000 without requiring any need for the operator to change the blade housing diameter from the preset blade housing diameter BHD1 for operating clearance adjustment purposes. Additionally, the cam mechanism 6900 consistently sets the blade housing diameter to the single, reproducible diameter, namely, the blade housing diameter BHD1, when the cam mechanism 6900 is in the first closed position 6999. Therefore, even if the annular rotary knife blade 6300 must be removed during the course of a work shift for replacement, sharpening, or cleaning purposes, upon reassembly and movement of the cam mechanism 6900 to the first, closed position 6998, blade housing diameter is reset the predetermined, desired diameter and, thus, the operating clearance between the rotary knife blade 6300 and the blade housing 6800 is returned to the predetermined, desired operating clearance, Under certain conditions, the cam mechanism 6900, in conjunction with the extended wear capability of the double axial blade—blade housing bearing structure 6550 of the assembled blade—blade housing combination 6500 allows for a "set it and forget it" mode of operation of the power operated rotary knife 6000, allowing for greater operator efficiency and less operator downtime during a work shift by avoidance of operator adjustments to operating clearance.

Because of the sliding blade—blade housing bearing interface 6550 between the rotary knife blade 6300 and the split blade housing 6800 in the assembled combination 6500 of the power operated rotary knife 6000, as would be recognized by one of skill in the art, running or operating clearance between the rotary knife blade 6300 and the blade housing 6800 must be provided to allow the rotary knife blade 6300 to rotate relatively freely within the annular blade support section 6850 of the split blade housing 6800. Actual running clearance will depend on a number of factors including the cutting or trimming application, the amount of time of use and the degree of wear of various components of the power operated rotary knife 6000 include the rotary knife blade 6300 and the blade housing 6800, the extent and type of lubrication provided in the blade—blade housing bearing interface region. However, running clearance typically is on the order of a 0.005 - 0.010 in. radial clearance or gap between the rotary knife blade 6300 and the blade housing 6800.

Handle Assembly 6110

As best seen in FIGS. 1-6 and 8-9, the handle assembly 6110 is similar in structure and function to the handle assembly 110 of the power operated rotary knife 100 of the first exemplary embodiment, as described in the '207 application. The handle assembly 6110 extends longitudinally from the head assembly 6200 in the rearward direction RW along the handle assembly central longitudinal axis LA. The handle assembly 6110 includes the central throughbore 6115 that extends from and through a proximal end of the handle assembly 6110 to the distal end 6112 of the handle assembly 6110. The throughbore 6115 is centered about the central longitudinal axis LA of the handle assembly 6110. The handle assembly 6110 includes a central core 6152 that defines a portion of the throughbore 6115. The central core 6152 supports an overlying hand piece 6120 that defines a gripping surface for the operator of the power operated rotary knife 6000. A threaded outer surface 6162 of a forward portion of the central core 6152 threads into a mating threaded proximal portion 6286 of an inner surface 6284 of a cylindrical annular boss 6280 of the frame body 6250 to secure the handle assembly 6110 to the frame body 6250 of the head assembly 6250.

Frame Body 6250

As best seen in FIGS. 1-6 and 8-9, the frame body 6250 includes the forward or distal portion 6251, which supports the blade housing assembly 6700, and the rearward or proximal portion 6280, extending in the rearward direction RW toward the handle assembly 6110. The rearward portion 6280 of the frame body 6250 includes the cylindrical annular boss 6282. As noted above, the cylindrical annular boss 6282 includes the inner surface 6284 having the threaded proximal portion 6286 which receives the threaded outer surface 6162 of the forward portion of the handle assembly central core 6152 to secure the head assembly 6200 to the handle assembly 6110. The rearward portion 6280 of the frame body 6250 is similar in function and structure to the rearward portion 280 of the frame body 250 of the power operated rotary knife 100 of the first exemplary embodiment, as described in the '207 application.

The frame body 6250 includes a throughbore 6290 which is generally aligned with the central throughbore 6115 of the handle assembly 6110 and extends along the handle assembly longitudinal axis L.A. The rearward portion 6280 includes the cylindrical annular boss 6282 having the threaded proximal portion 6286 of an inner surface 6284 which receives a threaded outer surface 6162 of the central core 6152 of the handle assembly 6112. The forward portion 6251 of the frame body 6250 receives and removably supports both a pinion gear shield 6297 and the blade—blade housing combination 6500, including the cam mechanism 6900 which is part of the blade housing assembly 6700. The pinion gear shield 6297 helps locate a drive gear assembly 6210 of a drive mechanism 6600 (similar to the drive gear assembly 210 of the drive mechanism 600 of the first exemplary embodiment of the '207 application), including a pinion gear 6610 and a sleeve bushing 6630. In this way, the frame body 6250 releasably and operatively couples the drive gear assembly 6210 to the assembled blade—blade housing combination 6500 such that the pinion gear 6610 of the gear train 6604 of the drive gear assembly 6210 operatively engages the driven gear 6340 of the annular rotary knife blade 6300 to rotate the knife blade 6300 with respect to the blade housing 6400 about the axis of rotation R.

The forward portion 6251 of the frame body 6250 includes a central cylindrical region 6254, an upper surface 6260 and a planar lower surface 6270. The planar lower surface 6270, best seen in FIG. 9, defines a planar mounting pedestal 6272 for affixing the assembled blade—blade housing combination 6500 to the frame body 6250. The throughbore 6290 of the frame body 6250 includes a forward cylindrical cavity 6290a defined by the central cylindrical region 6254 of the forward portion 6251 of the frame body 6250 and a rearward cylindrical opening 6290b defined by the cylindrical annular boss 6282 of the rearward portion 6280. The forward wall 6252 of the forward portion 6251 of the frame body 6250 defines an arcuate mounting surface 6252a. A pair of threaded openings 6252b positioned on opposite sides of the forward cylindrical cavity 6290a of the throughbore 6290 extend into the forward wall arcuate mounting surface 6252a. A pair of threaded fasteners 6299a pass through respective openings 6299b in the pinion gear shield 6297 to secure the pinion gear shield 6297 to the forward wall 6252 of the frame body 6250.

The planar lower surface 6270 of the forward portion 6251 of the frame body 6250 is substantially parallel to and offset below the handle assembly longitudinal axis LA. The planar lower surface 6270 includes a pair of threaded openings 6274, which are part of the planar mounting pedestal 6272 defined by the lower surface 6270. The threaded openings 6274 which are orthogonal in direction to the general extent of the planar lower surface 6270, receive a pair of threaded fasteners 6990. The fasteners 6990 include enlarged head portions 6991, unthreaded shaft portions 6992, and threaded end portions 6993. The threaded end portions 6993 of the fasteners 6990 are received in the threaded openings 6274 of the planar lower surface 6270 to secure assembled blade—blade housing combination 6500 to the frame body 6250. As the threaded fasteners 6990 of the cam mechanism 6900 are tightened into the threaded openings 6274 of the planar mounting pedestal 6272 of the frame body 6250, the respective heads 6991 of the threaded fasteners 6990 bear against the cam plate 6950 of the cam mechanism 6900, which, in turn, bears against a planar lower surface 6810a of the mounting section 6802 of the blade housing 6800. Thus, tightening of the threaded fasteners 6990 sandwiches and affixes the mounting section 6802 of the blade housing 6800 to the frame body 6250. That is, as best seen in FIGS. 2 and 4-6, when the threaded fasteners 6990 are tightened into the threaded openings 6274 of the planar mounting pedestal 6272, a planar upper surface 6808a of the blade housing mounting section 6802 is in bearing contact with and secured to the planar mounting pedestal 6272 of the lower surface 6270 of the frame body 6250. The mounting plate 6950 of the cam mechanism 6900, in turn, bears against the planar lower surface 6810a of the mounting section 6802 of the blade housing 6800 and is coupled to the planar mounting pedestal 6272 of the lower surface 6270 of the frame body 6250. This securing of the blade housing assembly 6700 to the frame body 6250 also secures the assembled blade—blade housing combination 6500, including the rotary knife blade 6300, to the frame body 6250 and properly positions the rotary knife blade 6300 to be rotatably driven about the central axis of rotation R by the gear train 6604 of the drive mechanism 6600 of the power operated rotary knife 6000.

Advantageously, because the unthreaded shaft portion 6992 of the pair of threaded fasteners 6990 pass through generally oval shaped first and second mounting slots 6826, 6836 (FIGS. 10, 22 and 24) which are larger in extent than the respective diameters of the shaft portions 6992 of the threaded fasteners 6990, the blade housing 6800, even though secured to the frame body lower surface 6270, is sufficiently free to move circumferentially such that the blade housing diameter is changed between the first blade housing diameter BHD1 when the cam mechanism 6900 is in the first, closed position 6998 (corresponding to the first, blade supporting position 6898 of the blade housing 6800) and the second blade housing diameter BHD2 when the cam mechanism 6900 is in the second, open position 6999 (corresponding to the second, blade changing position 6898 of the blade housing 6800). Since the pair of threaded fasteners 6990 tread into the threaded openings 6274 of the planar lower surface 6270 of the frame body 6250, the fasteners 6990 (and the cam mechanism mounting plate 6950) are fixed with respect to the frame body 6250 and thus are stationary with respect to the blade housing 6800. Under action of the cam member 6210 of the cam mechanism 6900 moving from the first, closed position 6998 (FIGS. 21 and 22) to the second, open position 6999 (FIGS. 23 and 24), the blade housing 6800 is moved circumferentially from the first blade housing diameter BHD1 when the cam mechanism 6900 is in the first, closed position 6998 to the second blade housing diameter BHD2 when the cam mechanism 6900 is in the second, open position 6999. The fact that the oval shaped first and second mounting slots 6826, 6836 are larger in extent than the respective diameters of the shaft portions 6992 of the threaded fasteners 6990 allows this circumferential movement the blade housing 6800 between the first blade housing diameter BHD1 and the second blade housing diameter BHD2 while the blade housing 6800 remains secured to the frame body 6250. Specifically, in the first, closed position 6998 of the cam mechanism 6900, the blade housing mounting slots 6826, 6836 are positioned with respect to the pair of fasteners 6990 such that the unthreaded shaft portions 6992 of the pair of fasteners 6990 are adjacent respective first ends 6826a, 6836a of the blade housing mounting slots 6826, 6836, corresponding to the blade housing 6800 being in the unexpanded blade housing diameter BHD1. By contrast, in the first, open position 6998 of the cam mechanism 6900, the blade housing mounting slots 6826, 6836 are positioned with respect to the pair of fasteners 6990 such that the unthreaded shaft portions 6992 of the pair of fasteners 6990 are adjacent respective second ends 6826b, 6836b of the blade housing mounting slots 6826, 6836, corresponding to the blade housing 6800 being in the expanded blade housing diameter BHD2.

As can best be seen in FIGS. 6 and 8-9, the frame body throughbore 6290 receives and supports the drive gear assembly 6210 of the head assembly 6200, which is part of the drive mechanism 6600 of the power operated rotary knife 6000. Specifically, the drive gear assembly 6210 includes the sleeve bushing 6630 which is received in the forward cylindrical cavity 6290a of the central cylindrical region 6254 of the forward portion 6251 of the frame body 6250. In turn, the pinion gear 6610 of the drive gear assembly 6210 is rotatably supported by the sleeve bushing 6630 such that the pinion gear 6610, when driven by the drive fitting of the flexible shaft drive assembly (not shown, but similar to the flexible shaft drive assembly 700 of the first exemplary embodiment of the '207 application) rotates about the pinion gear axis of rotation PGR, which is substantially coincident with the handle assembly longitudinal axis LA. A gear head 6614 of the pinion gear 6610 is operatively connected to the rotary knife blade driven gear 6340 such that a plurality of gear teeth 6615 of the gear head 6614 of the pinion gear 6610 mesh with and rotationally drive a mating plurality of gear teeth 6341 of the driven gear 6340 of the rotary knife blade 6300 to rotate the rotary knife blade 6300 about its central axis of rotation R.

Annular Rotary Knife Blade 6300

As can best be seen in FIGS. 6-9, the annular rotary knife blade 6300 is generally similar in structure and function to the annular rotary knife blade 2300 of the power operated rotary knife 2000 of the third exemplary embodiment of the '207 application including the blade bearing region 6320 of the annular blade body 6310 which is similar in structure and function to the blade bearing region 2320 of the annular blade body 2310 of the rotary knife blade 2300 of the third exemplary embodiment of the '207 application.

The blade style of the rotary knife blade 6300 is referred to as a straight blade style. Generally, differences in blade style (e.g., straight blade style, flat blade style, hook blade style and variations and combinations thereof) relate to the structure of the respective lower blade sections. While the exemplary rotary knife blade 6300 of the sixth exemplary embodiment is a straight blade style rotary knife blade, numerous other blade styles, including, but not limited to, hook and flat style blades and combinations of blade styles may be utilized, with an appropriate blade housing assembly 6700, in the power operated rotary knife 6000 of the present disclosure, as would be understood by one of skill in the art, it is the intent of the present disclosure to cover all such rotary knife blade styles and sizes and the corresponding blade housings, that may be used in the power operated rotary knife 6000.

The annular rotary knife blade 6300 of the power operated rotary knife 6000 includes the annular upper body or body section 6310 and the lower blade section 6360 extending from the body 6310. The rotary knife blade 6300 is supported for rotation about the central axis of rotation R by the blade housing 6800 and a cutting edge 6361 of the blade section 6360 defines the cutting plane CP (FIGS. 6 and 7) of the rotary knife blade 6300. The cutting plane CP is substantially orthogonal to the central axis of rotation R.

The annular rotary knife blade 6300 includes an upper end or first end 6302 and an axially spaced apart lower end or second end 6304, defining the cutting edge 6361 of the blade 6300, and an inner wall 6306 and a radially spaced apart outer wall 6308. The blade section 6360 of the rotary knife blade 6300 includes an upper end 6362, defined by a discontinuity or knee 6362a in an outer wall 6368 of the blade section 6360, and a lower end 6364, which is coincident with the blade cutting edge 6361, the cutting plane CP and the lower end 6304 of the rotary knife blade 6300. The blade section 6360 also includes the inner wall 6366 and the radially spaced apart outer wall 6368.

Turning to the annular body 6310 of the annular rotary knife blade 6300, the body 6310 includes the driven gear 6340, similar to the driven gear 2340 of the rotary knife blade 2300 of the third exemplary embodiment of the '207 application, defining a driven gear region 6340a of the annular and the bearing region 6320, similar to the bearing region 2320 of the rotary knife blade 2300 of the third exemplary embodiment. As best seen in FIG. 7, the body 6320 includes an upper end 6312 and an axially spaced apart lower end 6344 and an inner wall 6316 and a radially spaced apart outer wall 6318. The bearing region 6320 of the annular rotary knife blade 6300 includes a first bearing surface 6322 and an axially spaced second bearing surface 6382. The first and second bearing surfaces 6322, 6382 are both part of the outer wall 6318 of the annular rotary knife blade body 6310. The first bearing surface 6322 is defined by an upper bearing bead 6311 of the body 6310 and at least a portion of the first bearing surface 6322 is defined by an outer surface 6340b of the driven gear 6340. The second bearing surface 6383 is defined by a radially inwardly extending bearing race 6380.

Like the rotary knife blade 2300 and the annular blade housing 2400 of the assembled combination 2500 of the power operated rotary knife 2000 of the third exemplary embodiment of the '207 application, the assembled combination 6500 of the rotary knife blade 6300 and the annular blade housing 6800 comprises the blade—blade housing bearing structure 6550 that includes the first blade—blade housing bearing structure 6560 and the second blade—blade housing bearing structure 6570. In the power operated rotary knife 2000 of the third exemplary embodiment, the first blade—blade housing bearing structure 2560 included the first arcuate bearing surface 2322 of the bearing region 2320 of the rotary knife blade 2300 engaging and bearing against the first arcuate bearing surface 2462 of the bearing region 2460 of the blade support section 2450 of the annular blade housing 2400. The first blade—blade housing bearing structure 6560 of the power operated rotary knife 6000 has substantially the same structure, namely, the first blade—blade housing bearing structure 6560 includes the first arcuate bearing surface 6322 of the bearing region 6320 of the rotary knife blade 6300 which engages and bears against a first arcuate bearing surface 6862, defined by a bearing race 6866, of a bearing region 6860 of a blade support section 6850 of the annular blade housing 6800. In the power operated rotary knife 2000 of the third exemplary embodiment, the second blade—blade housing bearing structure 2570 included the second bearing surface 2382 of the bearing region 2320, defined by the bearing race 2380, of the rotary knife blade 2300 engaging and bearing against the second bearing surface 2482, defined by the bearing bead 2480, of the blade support section 2450 of the annular blade housing 2400. Similarly, the second blade—blade housing bearing structure 6570 of the power operated rotary knife 6000 has substantially the same structure, namely, a second bearing surface 6382 of the bearing region 6320, defined by the bearing race 6380, of the rotary knife blade 6300 engages and bears against a second bearing surface 6882 of a bearing region 6880, defined by a bearing head 6880, of the blade support section 6850 of the annular blade housing 6800.

Blade Housing Assembly 6700

The blade housing assembly 6700 includes the annular split ring blade housing 6800 (FIGS. 10, 11 and 25) and the cam mechanism 6900 (FIGS. 12-15). As explained above, and as schematically depicted in FIGS. 11-14, rotation of the cam member 6910 of the cam mechanism 6900 about its axis of rotation CMA from the first, closed position 6998 to the second, open position 6999 of the cam mechanism 6900 increases the width of the split 6801a from the first blade housing gap or split distance D1 to the second blade housing split distance D2 between opposing faces 6825, 6835 of the first and second body portions 6820, 6840 of the blade housing mounting section 6802 and thereby moves the blade housing 6800 from the first, blade supporting position 6898 of the blade housing 6800 to the second, blade changing position 6899 of the blade housing 6800. Conversely, rotation of the cam member 6910 of the cam mechanism 6900 about its axis of rotation CMA from the second, open position 6999 to the first, closed position 6999 decreases the width of the split 6801a from the second blade housing gap or split distance D2 to the first blade housing split distance D1 between opposing faces 6825, 6835 of the first and second body portions 6820, 6840 of the blade housing mounting section 6802 and thereby moves the blade housing 6800 from the second, blade changing position 6899 of the blade housing 6800 to the first, blade supporting position 6898 of the blade housing 6800. As noted previously and as can be seen in FIGS. 10-11, 22 and 24, for purposes of uniformity, the blade housing split distances D1, D2 are measured between circumferentially spaced apart ends 6852a, 6852b of the inner wall 6852 of the blade support section 6850 of the blade housing 6800 adjacent the split 6801a.

Split Ring Blade Housing 6800

As best seen in FIGS. 7, 10, 11 and 25, the blade housing 6800 comprises the annular split ring 6801 including the split 6801a that extends radially through the annular blade support section 6850 and the mounting section 6802, that is, extending radially through a blade housing outer wall 6800b and a blade housing inner wall 6800a. The annular blade support section 6850 supports the annular rotary knife blade 6300 for rotation about the blade central axis of rotation R. The mounting section 6802 overlaps and extends radially outwardly from the blade support section 6850 and includes a generally planar mounting platform 6803 which is secured to the frame body 6250 by being sandwiched between an upper surface 6952 of the cam plate 6950 of the cam mechanism 6900 and the planar mounting pedestal 6272 defined by the lower surface 6370 of the forward portion 6251 of the frame body 6250. Specifically, the planar mounting platform 6803 is secured to the frame body 6250 by a pair of threaded fasteners 6990 of the cam mechanism 6900. The pair of threaded fasteners 6990 extending through aligned openings 6982a, 6982b of the cam plate 6950 and aligned slots 6826, 6836 of the blade housing mounting section 6802 and thread into a pair of threaded openings 6274 formed in the lower surface 6370 of the forward portion 6251 of the frame body 6250. As the pair of threaded fasteners 6990 are tightened, the planar mounting platform 6803 is sandwiched between the cam plate 6950 of the cam mechanism 6900 and the planar mounting pedestal 6272 of the frame body 6250 and thereby secured to the frame body 6250.

The annular split blade housing 6800 includes the inner wall 6800a and the radially spaced apart outer wall 6800b and an upper end 6800c and an axially spaced apart lower end 6800e, The upper end 6800c of the blade housing 6800, which includes respective upper surfaces 6808a, 6856a of both the radially extending mounting section 6802 and the annular blade support section 6850, defines a generally planar upper surface 6808a of the blade housing 6800. The lower end 6800e of the blade housing 6800, which includes respective lower surfaces 6810a, 6858a of both the mounting section 6802 and the blade support section 6850, defines a generally planar lower surface 6800f of the blade housing 6800. The annular blade support section 6850 of the blade housing 6800 is similar to the annular blade support section 2450 of the blade housing 2400 of the third exemplary embodiment and reference is made to the description of the blade support section 2450 in the '207 application for additional details of the structure and function of the blade support section 6850. The blade support section 6850 includes an inner wall 6852, which comprises and corresponds to the inner wall 6800a of the blade housing 6800, and a radially spaced apart outer wall 6854, which defines a portion of the outer wall 6800b of the blade housing 6800, and the upper end 6856, which defines a portion of the upper end 6800c of the blade housing 6800, and the axially spaced apart lower end, which defines a portion of the lower end 6800e of the blade housing 6800.

As can best be seen in FIG. 7, the inner wall 6852 of the blade support section 6850 defines the bearing region 6860 of the blade housing 6800, which is similar in structure and function to the bearing region 2460 of the blade support section 2450 of the blade housing 2400 of the third exemplary embodiment. The hearing region 6860 of the blade support section 6850 includes a bearing race 6866 comprising the arcuate first bearing surface 6862 and a bearing bead 6880 comprising a second bearing surface 6882 of the bearing region 6860. The bearing region 6860 of the blade housing 6800 engages a bearing region 6320 of the body 6310 of the rotary knife blade 6300 to support the blade 6300 for rotation about the central axis of rotation R. The inner wall 6852 of the blade support section 6850 defines a blade housing central opening BHCO (FIGS. 9 and 10) and is centered about and defines the blade housing center line CBH. The blade housing center line CBH, in the first, blade supporting position 6898 of the blade housing 6800, is substantially coincident with the blade central axis of rotation R. A circumference defined by the outer wall 6854 of the blade support section 6850 plus the split width or split distance D1 defines the blade housing diameter BHD1 in the first, blade supporting position 6898 of the blade housing 6800, while a circumference defined by the outer wall 6854 plus the split width or split distance D2 defines the blade housing diameter BHD2 in the second, blade changing position 6899 of the blade housing 6800. In the second, blade changing position 6899 of the blade housing 6800, the inner wall 6852 of the blade support section 6850 takes on a very slight oval or egg-shaped configuration because of the larger split width D2.

As can best be seen in FIGS. 10 and 11, the mounting section 6802 of the blade housing 6800 includes an inner wall 6804, which overlaps and is coincident with the inner wall 6852 of the blade support section 6850 and comprises and corresponds to a portion of the inner wall 6800a of the blade housing 6800, and a radially spaced apart outer wall 6806, which defines a portion of the outer wall 6800b of the blade housing 6800, and an upper end 6808, which defines a portion of the upper end 6800e of the blade housing 6800, and an axially spaced apart lower end 6810, which defines a portion of the lower end 6800e of the blade housing 6800. The upper end 6808 of the mounting section 6802 defines the generally planar upper surface 6808a. The upper end 6856 (defining the upper planar surface 6856a) of the blade support section 6850 and the upper end 6808 (defining the upper planar surface 6808a) of the mounting section 6802 are advantageously coplanar with and together form the planar upper surface 6800d of the blade housing 6800. A first arcuate recess 6815 is formed in the planar upper surface 6808a of the upper end 6808 adjacent the inner wall 6800a of the blade housing 6800. The first arcuate recess 6815 provides clearance for the gear head 6624 of the pinion gear 6610 such that the pinion gear gear head 6624 is positioned to engage the mating driven gear 6340 of the rotary knife blade 6300. A second, shallower arcuate recess 6816 formed in the planar upper surface 6808a of the upper end 6808 adjacent the inner wall 6800a of the blade housing 6800 is positioned radially outwardly from and aligned with the first arcuate recess 6815 and provides clearance for the sleeve bushing 6630 that supports the pinion gear 6610 for rotation about its pinion gear axis of rotation PGR. The first arcuate recess 6815 circumferentially interrupts the arcuate first bearing surface 6862 of the bearing region 6860 of the blade housing blade support section 6850. The first and second arcuate recesses 6815, 6816, in turn, are bisected by the radially extending blade housing split 6801a which extends through the inner wall 6800a of the blade housing 6800.

The lower end 6810 of the mounting section 6802 defines the generally planar lower surface 6810a and the lower end 6858 (defining the lower planar surface 6858a) are advantageously coplanar with and together form the planar lower surface 6800f of the blade housing 6800. That is, as can best be seen in FIG. 25, the upper and lower surfaces 6800d, 6800f define parallel planes providing the blade housing with a smooth profile having substantially parallel upper and lower planar surfaces and uniform thickness in both the blade support section 6850 and the mounting section 6802 of the blade housing 6800. That is, the planar mounting platform 6803 of the mounting section 6202 is substantially the same thickness as the thickness of the blade support section 6850 as measured axially, that is, in a direction, substantially orthogonal to the blade housing split axis BHSA and substantially parallel to the blade housing center line CBH.

Extending between circumferentially spaced apart first and second ends 6812, 6814 of the mounting section 6802 is the central region 6811 of the mounting section 6802. The split 6801a of the blade housing 6800 divides or bisects the central region 6811 defining the first body portion 6820 and the second body portion 6830 separated along the blade housing split axis BHSA by the split distance, which, as measured at the inner wall 6852 of the blade support section 6850, in the first, blade supporting position 6898 of the blade housing 6800 is split distance D1 and, in the second, blade changing position 6899 of the blade housing 6800 is split distance D2. The first body portion 6820 of the blade housing central region 6811 includes a generally planar upper surface 6821, an axially spaced apart, generally planar lower surface 6822. The first body portion 6820 also includes an inner surface 6823 forming part of: a) the inner wall 6800a of the blade housing 6800; b) the inner wall 6804 of the mounting section 6802; and c) the coincident inner wall 6852 of the blade support section 6850, and an outer surface 6824 forming part of; a) the outer wall 6800b of the blade housing 6800; and b) the outer wall 6806 of the mounting section 6802. The second body portion 6830 of the blade housing central region 6811 includes a generally planar upper surface 6831, an axially spaced apart, generally planar lower surface 6832. The second body portion 6830 also includes an inner surface 6833 forming part of: a) the inner wall 6800a of the blade housing 6800; b) the inner wall 6804 of the mounting section 6802; and c) the coincident inner wall 6852 of the blade support section 6850, and an outer surface 6834 forming part of: a) the outer wall 6800b of the blade housing 6800; and b) the outer wall 6806 of the mounting section 6802.

Opposing facing surfaces 6825, 6835 of the first and second body portions 6820, 6830 define the blade housing split 6801a. The first body portion 6820 includes the generally oval shaped first mounting slot 6826 extending between and through the upper and lower surfaces 6821, 6822, while the second body portion 6830 includes the generally oval second mounting slot 6836 extending between. and through the upper and lower surfaces 6831, 6832. The unthreaded shaft portions 6992 of the pair of threaded fasteners 6990 of the cam mechanism 6900 pass through the respective mounting slots 6826, 6836 of first and second body portions 6820, 6830 of the central region 6811 of the mounting section 6802 of the blade housing 6800. The unthreaded shaft portions 6992 of pair of threaded fasteners 6990 are captured in respective cam plate openings 6982a, 6982b of the cam plate 6950 and the enlarged heads 6991 of the pair of fasteners 6990 bear against the cam plate 6950. The unthreaded shaft portions 6992 of the pair of threaded fasteners 6990 pass through the respective mounting slots 6826, 6836 of first and second body portions 6820, 6830 and the threaded end portions 6993 of the pair of fasteners 6990 then thread into respective threaded openings 6274 of the planar mount pedestal 6272 of the lower surface 6270 of the fame body 6250 to secure the blade housing 6800 to the frame body 6250. An upper surface 6952 of the cam plate 6950 bears against the planar lower surface 6810a of the blade housing mounting section 6802, specifically, the planar lower surfaces 6822, 6832 of the first and second body portions 6820, 6830 of the blade housing mounting section 6802, to urge the planar upper surface 6808a of the mounting section 6802 against the planar mounting pedestal 6272 of the lower surface 6270 of the fame body 6250 and secure the blade housing 6800 to the frame body 6250.

The lower surface 6822 of the first body portion 6820 includes a first cam slot 6827 which receives and constrains a first cam pin 6930 of the cam member 6910 of the cam mechanism 6900. The first cam slot 6827 includes a first end portion 6827a and a second end portion 6827b that is closer to the split 6801a. The first cam slot 6827 includes a linear portion 6828 defining a linear path of travel 6828a for the first cam pin 6930 and an offset catch portion 6829, The first cam slot 6827 is transverse to the blade housing split axis BHSA and, if extended along the linear path of travel 6828a, would intersect the blade housing split 6801a. The lower surface 6832 of the second body portion 6830 includes a second cam slot 6837 which receives and constrains a second cam pin 6932 of the cam member 6910 of the cam mechanism 6900. The second cam slot 6837 includes a first end portion 6837a and a second end portion 6837b that is closer to the split 6801*a*. The second cam slot 6837 includes a linear portion 6838 defining a linear path of travel 6838*a* for the first cam pin 6930 and an offset catch portion 6829. The second cam slot 6827 is transverse to the blade housing split axis BHSA and, if extended along the linear path of travel 6838*a*, would intersect the blade housing split 6801*a*.

In the first, closed position 6998 of the cam mechanism 6900, the first cam pin 6930 is positioned or located nearer the first end portion 6827*a* of the first cam slot 6927 and the second cam pin 6932 is positioned or located nearer the first end portion 6837*a* of the second cam slot 6937. In one exemplary embodiment, the first cam pin 6930 is positioned at the first end portion 6827*a* of the first cam slot 6927 and the second cam pin 6932 is positioned at the first end portion 6837*a* of the second cam slot 6937. Also, in the first, closed position 6998 of the cam mechanism 6900, the unthreaded shaft portions 6992 of the pair of fasteners 6990 are positioned in proximity to or adjacent respective first ends 6826*a*, 6836*a* of the blade housing mounting slots 6826, 6836. As the cam member 6910 is rotated to the second, open position 6999, the first and second cam pins 6932 move or translate within their respective first and second cam slots 6827, 6837 along the respective linear paths of travel 6928*a*, 6938*a* to positions or locations nearer the respective second end portions 6827*b*, 6837*b* of the cam slots 6827, 6837, coming to rest in the respective offset catch portions 6829, 6839. This movement or translation of the first and second cam pins 6932 within their respective first and second cam slots 6827, 6837 from the respective first end portions 6827*a*, 6837*a* to the respective second end portions 6827*b*, 6837*b* forces, by camming action, an expansion of the blade housing diameter from the unexpanded blade housing diameter BHD1, corresponding to the first, blade supporting position 6898 of the blade housing 6800, to the expanded blade housing diameter BHD2, corresponding to the second, blade changing position 6899 of the blade housing 6800, allowing for easy removal of the annular rotary knife blade 6300 from the blade housing blade support section 6850. Further, as the first and second body portions 6820, 6830 of the blade housing mounting section 6802 move apart or spread circumferentially along the blade housing split 6801*a* such that the blade housing diameter moves from the unexpanded blade housing diameter BHD1 to the expanded blade housing diameter BHD2, the unthreaded shaft portions 6992 of the pair of fasteners 6990 are now in proximity to or adjacent respective second ends 6826*b*, 6836*b* of the blade housing mounting slots 6826, 6836.

Conversely, as the cam member 6910 is rotated from the second, open position 6999 to the first, closed position 6998, the first and second cam pins 6930, 6932 move or translate within their respective first and second caner slots 6827, 6837 along the respective linear paths of travel 6928*a*, 6938*a* to positions nearer the respective first end portions 6827*a*, 6837*a*. This movement or translation of the first and second cam pins 6930, 6932 within their respective first and second cam slots 6827, 6837 from the respective second end portions 6827*b*, 6837*b* to the respective first end portions 6827*a*, 6837*a* allows the blade housing 6800, which is resiliently deformable and has the unexpanded blade housing diameter BHD1 as its natural, undeformed condition, by camming action, to return from the expanded blade housing diameter BHD2 to the unexpanded blade housing diameter BHD1. Further, as the blade housing mounting section 6802 moves circumferentially to return to its unexpanded blade housing diameter BHD1 the unthreaded shaft portions 6992 of the pair of fasteners 6990 are once again in proximity to or adjacent respective first ends 6826*a*, 6836*a* of the blade housing mounting slots 6826, 6836.

In one exemplary embodiment, the thickness or depth of the blade housing 6800 is substantially uniform (ignoring the pinion gear and sleeve bushing recesses 6815, 6816 and the first and second cam slots 6827, 6837) along the entirety of the blade housing 6800 and is approximately 0.21 in. In one exemplary embodiment, a length of each of the facing surfaces of the first and second body portions 6820, 6830, as measured along the blade housing split axis BHSA, is approximately 0.63 in. A total width of the central region of the mounting section 6802, in the blade supporting position 6898 of the blade housing 6800, in one exemplary embodiment, is approximately 1.59 in. In one exemplary embodiment, the first and second oval mounting slots 6826, 6836 define an opening, as measured along the principal axis of the slots, of approximately 0.40 in. As can best be seen in FIG. 10, with respect to the linear portions 6828, 6838 of the first and second cam slots 6827, 6837, the linear portion 6828 of the first cam slot 6827, as measured along the linear path of travel 6828*a*, is approximately 0.36 in., while the linear portion 6838 the second cam slot 6837, as measured along the linear path of travel 6838*a*, is approximately 0.32 in. As noted previously, it is understood, that these dimensions will necessarily change based on the size and configuration, characteristics and parameters of the rotary knife blade to be supported by the blade housing, the blade—blade housing bearing structure, and other parameters and characteristics of the power operated rotary knife 6000 and components thereof.

Cam Mechanism 6900

As best seen in FIGS. 12-15, the cam mechanism 6900 includes the cam member 6910 supported for rotation shout the cam member axis of rotation CMA by the cam plate 6950. The cam member 6910 rotates between the first, closed or locked position 6999 causing the blade housing 6800 to be in the first, blade supporting position 6898 and the second, open or unlocked position 6999 causing the blade housing 6800 to be in the second, blade changing position 6899 having an increased diameter of the blade support section 6850 for the purpose of allowing the rotary knife blade 6300 to be released from the blade housing 6800.

Figure 19:
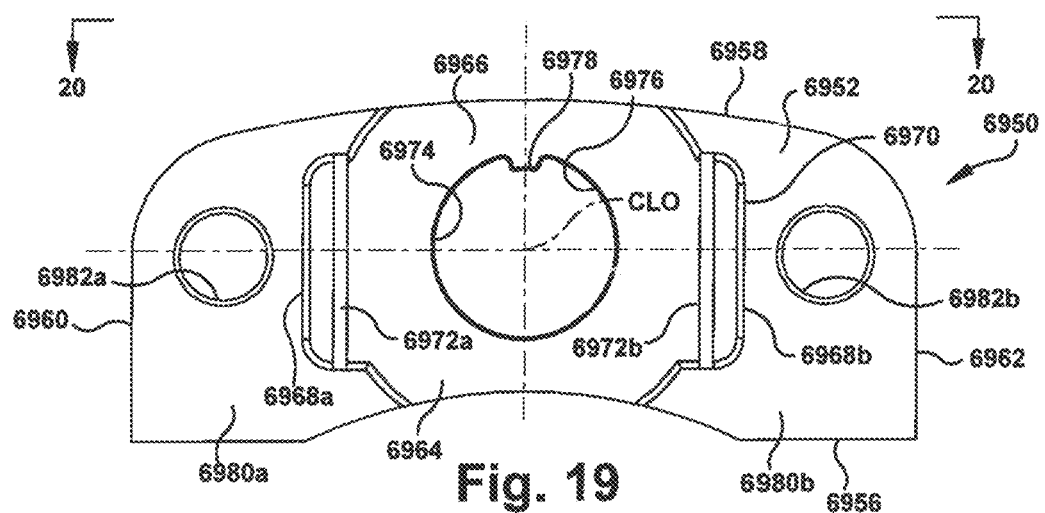
FIG. 19 is a schematic top plan view of a cam plate of the cam mechanism of FIG. 12.
Figure 20:
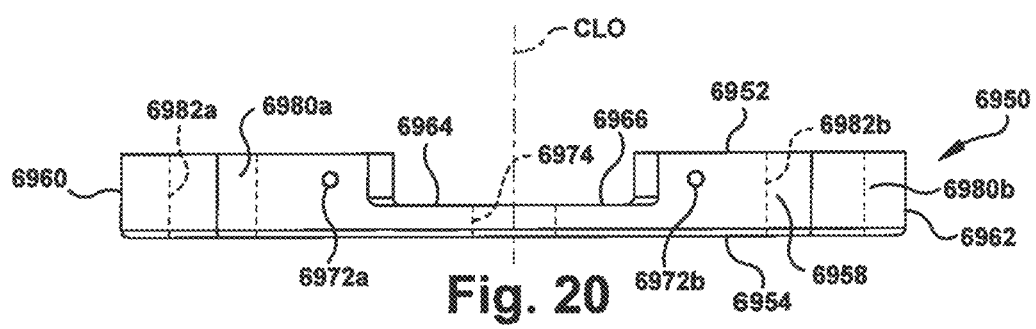
FIG. 20 is a schematic rear elevation view of the cam plate of FIG. 19.
Figure 21:
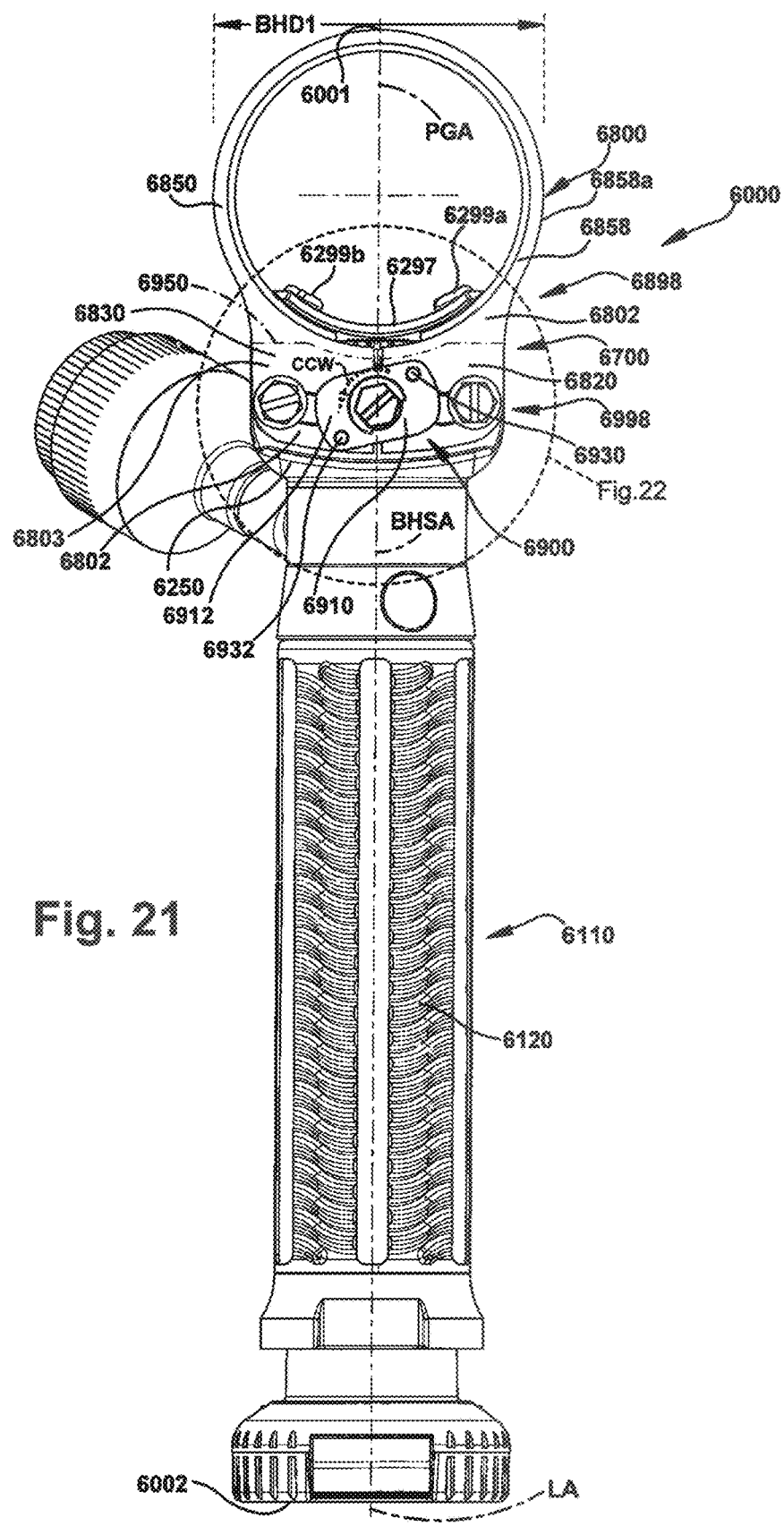
FIG. 21 is a schematic bottom plan view of the power operated rotary knife of FIG. 1 with the annular rotary knife blade removed and a cam plate of the cam mechanism of the blade housing assembly removed and with the cam mechanism in a first, closed position and the annular split blade housing in the first, blade supporting position.
Figure 22:
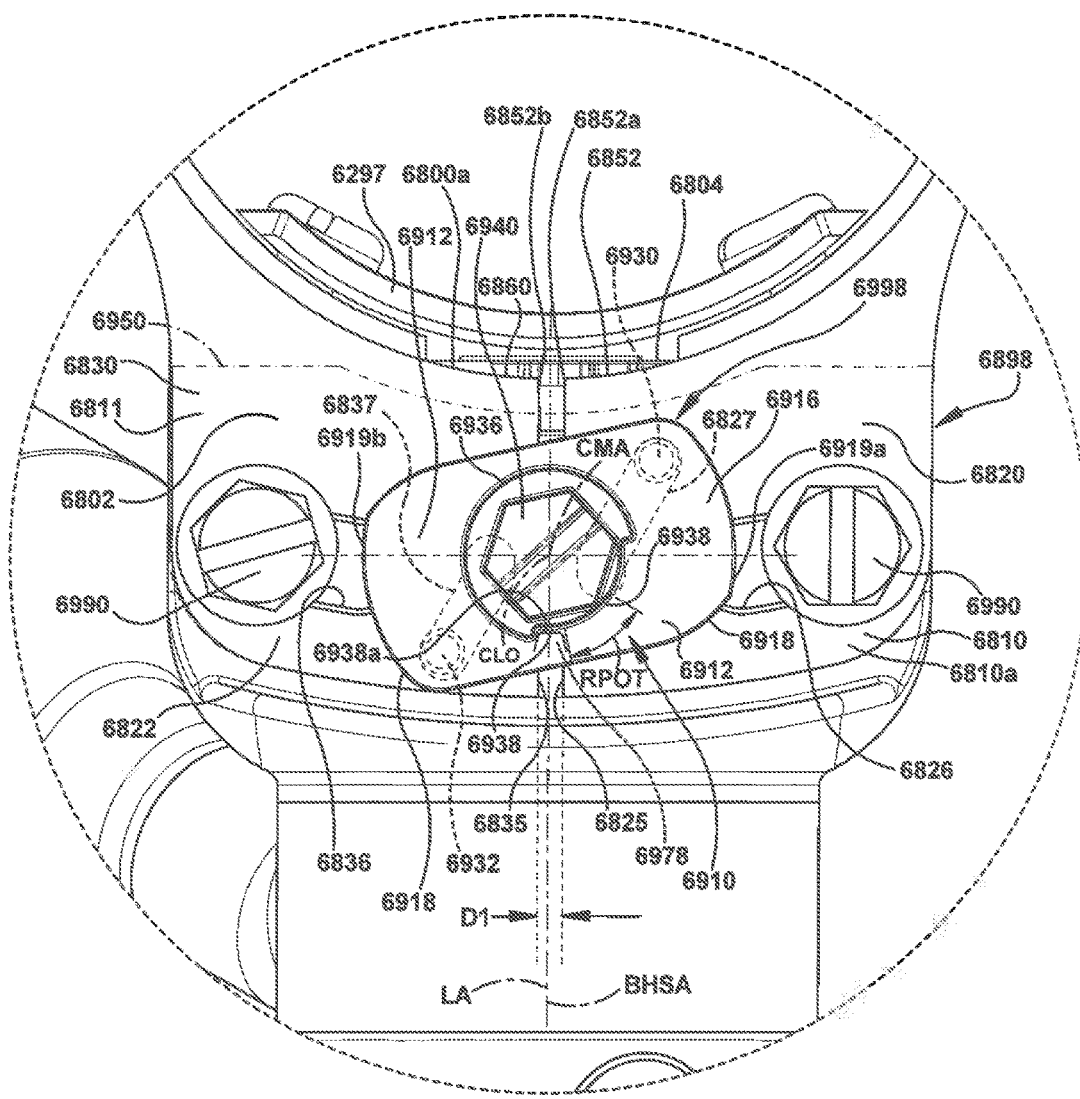
FIG. 22 is a schematic enlarged bottom plan view of a portion of the power operated rotary hide of FIG. 1 which is within a circle labeled FIG. 22 in FIG. 21, with the cam mechanism in the first, closed position and the annular split blade housing in the first, blade supporting position.

As best seen in FIGS. 19 and 20, the cam plate 6950 of the cam mechanism 6900 is generally rectangular in plan view and includes an upper surface 6952 and a spaced apart generally planar lower surface 6954. The upper and lower surfaces 6952, 6954 are spaced apart by a front side 6956, facing toward the annular rotary knife blade 6300, and a back side 6958, facing toward the handle assembly 6110. Extending between the front and back sides 6956, 6958 of the cam plate 6950 are first and second lateral sides 6960, 6962. The upper surface 6952 of the cam plate 6950 includes generally rectangular recess 6964 that receives and supports the cam member 6910. Positioned on either side of the recess 6964 are flanking portions 6980 of the cam plate 6950 that extend a full width or distance between the upper and lower surfaces 6952, 6954. The upper surface recess 6964 defines a seating region 6966 for the cam member 6910. The recess 6964 extends through the front and back Sides 6956, 6958 of the cam plate 6950. The recess 6964 is defined by a planar lower wall 6967 and two side walls 6968*a*, 6968*b* that extend from the front side 6956 to the back side 6958 of the cam plate 6950. The planar lower wall 6967 of the recess 6964 is generally parallel to and intermediate between the upper and lower surfaces 6952, 6954 of the cam plate. A centrally located opening 6974 extends through lower surface 6954 of the cam plate 6950 and intersects the recess

6964, passing though the planar lower wall 6967 of the recess 6964. The central opening 6974 receives an upper cylindrical portion 6936 of a downwardly extending boss 6934 of the cam member 6910. A center line CLO through the central opening 6974 defines and is coincident with the cam member axis of rotation CMA. An inner wall 6976 defines the central opening 6974 and includes a radially inwardly extending rotation limitation tab 6978 of the central opening 6974.

Advantageously, the rotation limitation tab 6978 is received in a cut out or arcuate notch 6938 in a side wall 6936 of the upper cylindrical portion 6935 of the downwardly extending boss 6934 of the cam member 6910 to limit rotation of the cam member 6910 with respect to the cam plate 6950. That is, because the tab 6978 of the cam plate 6950 extends into the arcuate notch 6938 of the cam member boss 6934, an arcuate or rotational path of travel RPOT of the cam member 6920 with respect to the cam plate 6950 is necessarily limited by the arcuate or circumferential extent of the arcuate notch 6938. When viewed in bottom plan view as shown, for example, in FIGS. 21-24, rotation of the cam member 6910 in the counterclockwise direction CCW (FIG. 21) (which would be a clockwise direction if viewed in top plan view, e.g., FIG. 3) is limited by the abutment of the first end 6938*a* of the arcuate notch 6938 of the cam member 6910 and the protruding tab 6978 of the cam plate 6950 (the tab 6978 schematically shown in dashed line in FIG. 22). Accordingly, in rotating the cam member 6910 from the second, open position 6999 to the first, closed position 6998, the engagement of the tab 6978 and the first end 6938*a* of the arcuate notch 6938 prevents over rotation of the cam member 6910. Rotation of the cam member 6910 in the clockwise direction CW (FIG. 23) from the first, closed position 6998 to the second, open position 6999 is limited by: a) the engagement of the first and second cam pins 6930, 6932 within the respective offset catch portions 6829, 6839 of the first and second cam slots 6827, 6837 of the first and second body portions 6920, 6930 of the blade housing mounting section 6802; and b) the abutment of the first and second fasteners 6990 of the cam mechanism 6900 with the second end portions 6826*b*, 6836*b* of the blade housing mounting slots 6826, 6836. During assembly of the cam member 6910 to the cam plate 6910 or disassembly of the cam member 6910 from the cam plate 6910, the abutment of the opposite or second end of the notch 6938 of the cam member 6910 and the protruding tab 6978 of the cam plate 6950 advantageously prevent over rotation of the cam member 6910 in the clockwise direction CW. Over rotation of the cam member 6910 with respect to the cam plate 6910 in the clockwise direction CW during assembly could result in the cam member rectangular base 6912 pushing against and permanently bending or deforming a pair of retainer springs 6972*a*, 6972*b* of the cam plate 6950. In one exemplary embodiment, the rotational path of travel RPOT of the cam member 6930 in moving between the first, closed position 6998 and the second, open position 6999 is approximately 45°.

Figure 17:
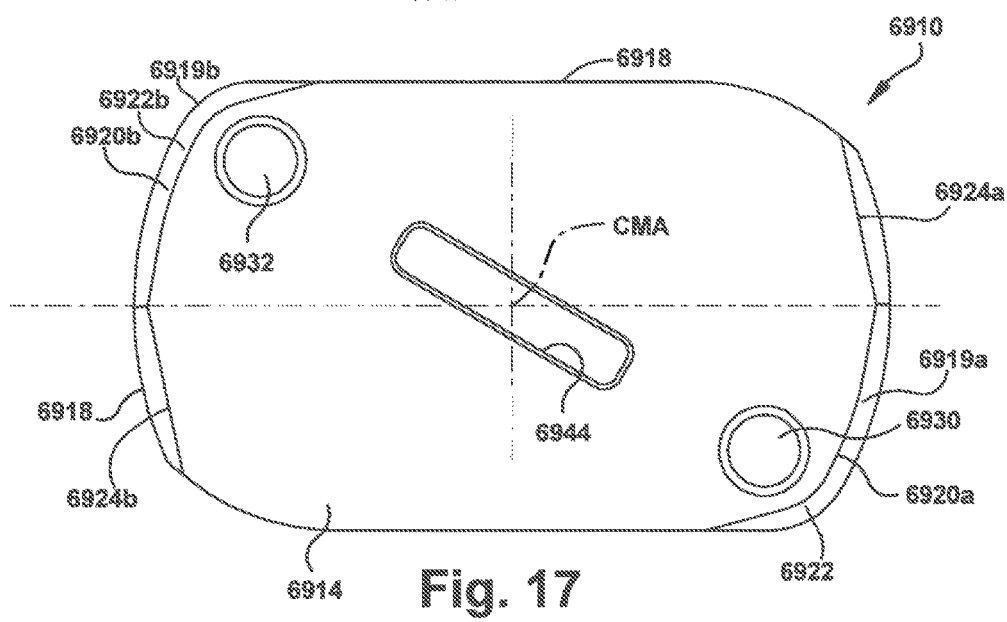
FIG. 17 is a schematic top plan view of the cam member of FIG. 16.
Figure 18:
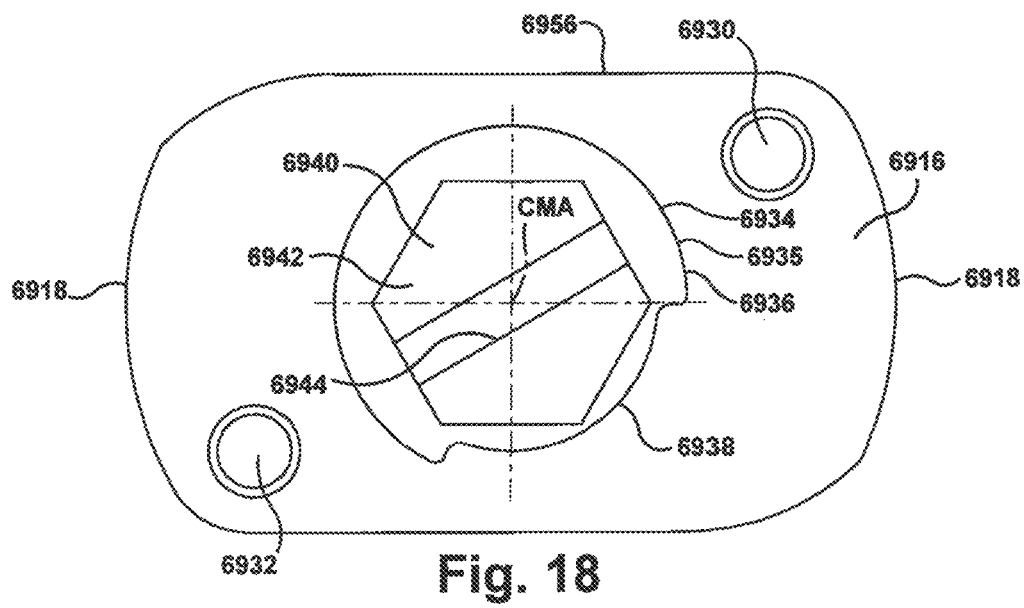
FIG. 18 is a schematic bottom plan view of the cam member of FIG. 16.

The side walls 6968*a*, 6968*b* of the recess 6964 in the upper surface 6952 of the cam plate 6950 includes respective outwardly bowed portions 6970*a*, 6970*b*, that is, outwardly bowed with respect to the center line CLO through the central opening 6974. Respective first and second retainer springs 6972*a*, 6972*b* spaced from and extending substantially parallel to the planar lower wall 6967 of the upper surface recess 6964 bridge the pair of outwardly bowed portions 6970*a*, 6970*b* of the side walls 6968*a*, 6968*b*. As can best be seen in FIGS. 13 and 15, the pair of retainer springs 6972*a*, 6972*b* bear against respective ledges 6922*a*, 6922*b* formed in recessed regions 6920*a*, 6920*b* of the side wall 6928 of a rectangular base 6912 of the cam member 6910 to maintain the cam member 6910 within the recess 6964 as the cam member 6910 is rotated between its first and second positions 6998, 6999. Additionally, in the first, closed or locked position 6998 of the cam member 6910, central portions 6973*a*, 6973*b* of the pair of retainer springs 6972*a*, 6972*b* bear against respective planar or flat areas 6924*a*, 6924*b* (best seen in FIGS. 13 and 17) of the recessed regions 6920*a*, 6920*b* of the side wall 6918 of the cam member base 6912, to reproducibly, consistently and precisely set the rotational position of the cam member 6910 in the first, closed position 6998 of the cam member and thereby reproducibly, consistently and precisely set the blade housing diameter BHD1 and the split distance D1 between opposing faces 6825, 6835 of the first and second body portions 6820, 6830 of the blade housing mounting section 6802 in the first, blade supporting position 6898 of the blade housing 6800, as further explained below.

The retainer springs 6972*a*, 6972*b* are disposed in respective horizontal openings in the cam plate 6950. The cam plate 6950 is staked to displace material over the horizontal openings to maintain the retainer springs 6972*a*, 6972*b* permanently in place. The flanking portions 6980*a*, 6980*b* of the cam plate 6950 includes respective ones of a pair of openings 6982*a*, 6982*b*. The pair of openings 6982*a*, 6982*b* each receive a respective one of a pair of threaded fasteners 6990. Each of the pair of threaded fasteners 6990 have a shank terminating in a threaded distal end portion. The respective shanks of the pair of threaded fasteners 6990 each include differing diameter portions between the threaded distal portions and a hexagonal head of the fasteners 6990 such that the fasteners 6990 are captured in and do not fall out of their respective openings 6982*a*, 6982*b*. The pair of fasteners 6990 function to secure the blade housing assembly 6700, including the blade housing 6800 and the cam mechanism 6800 to the frame body 6250 of the head assembly 6200. Specifically, the threaded fasteners 6990 pass through the respective cam plate openings 6982*a*, and also pass through respective mounting slots 6826, 6836 of first and second body portions 6820, 6830 of the central region 6811 of the mounting section 6802 of the blade housing 6800 and then thread into respective threaded openings 6274 of the planar mount pedestal 6272 of the lower surface 6270 of the fame body 6250. Thus, the blade housing 6800 is thereby secured to the frame body 6250 by having the blade housing mounting section 6802 being sandwiched between the cam plate 6950 of the cam mechanism 6900 and the planar mounting pedestal 6272 of the lower surface 6270 of the frame body 6250 as the fasteners 6990 are threaded into the threaded openings 6274 of the planar mount pedestal 6272 of the lower surface 6270 of the fame body 6250.

Because the mounting slots 6826, 6836 of the mounting section 6802 of the blade housing 6800 are oval shaped in top plan view, the mounting slots 6826, 6836 are longer, as viewed along the length of the respective slots 6826, 6836, than a diameter of the shanks of the threaded fasteners 6990 of the cam mechanism 6900. Advantageously, as the blade housing 6800 is moved by the cam mechanism 6900, the diameter of the blade support section 6850 between the first blade supporting position 6898, having a smaller diameter of the blade support section 6850, and the second blade changing position 6899, having a larger diameter of the blade support section 6850, the blade housing 6800 remains secured to the frame body 6250 by the sandwiching or bearing action of the cam plate 6950 bridging and bearing against the blade housing mounting section 6802 and urging the blade housing mounting section against the planar mounting pedestal 6272 of the frame body 6250. Stated another way, because the mounting slots 6826, 6836 of the blade housing mounting section 6802 are longer in extent than the diameter of the shanks of the threaded fasteners 6990, rotation of the cam member 6910 of the cam mechanism 6900 about its axis of rotation CMA from the first, closed position 6998 to the second, open position 6999 of the cam mechanism 6900 increases the width of the split 6801a from the first blade housing gap or split distance D1 to the second blade housing split distance D2 between opposing faces 6825, 6835 of the first and second body portions 6820, 6830 of the blade housing mounting section 6802 and thereby moves the blade housing 6800 from the first, blade supporting position 6898 to the second, blade changing position 6899 of the blade housing 6800, while the blade housing 6800 remains secured to the frame body 6250. Conversely, because the mounting slots 6826, 6836 of the blade housing mounting section 6802 are longer in extent or length than the diameter of the shanks of the threaded fasteners 6990, rotation of the cam member 6910 of the cam mechanism 6900 about its axis of rotation CMA from the second, open position 6999 to the first, closed position 6998 of the cam mechanism 6900 decreases the width of the split 6801a from the second blade housing gap or split distance D2 to the first blade housing split distance D1 between opposing faces 6825, 6835 of the first and second body portions 6820, 6830 of the blade housing mounting section 6802 and thereby moves the blade housing 6800 from the second, blade changing position 6896 to the first, blade supporting position 6898 of the blade housing 6800, again, while the blade housing 6800 remains secured to the frame body 6250.

As can best be seen in FIGS. 16-18 and 20-24, the cam member 6910 includes the rectangular base 6912 having a generally planar upper surface 6913 and a generally planar lower surface 6916 separated by the circumferentially extending side wall 6918. A pair of opposite, diagonally spaced apart portions 6919a, 6919b of the side wall 6918 include the recessed regions 6920a, 6920b. The recessed regions 6920a, 6920b define respective ledges 6922a, 6922b which, as explained previously, receive and bear against the pair of retainer springs 6972a, 6972b of the cam plate 6950 to maintain the cam member 6910 within the recess 6964 of the as the cam member 6910 is rotated between its first and second positions 6998, 6999. The recessed regions 6920a, 6920b of the side wall 6918 of the cam member base 6912 also include respective planar or flat areas 6924a, 6924b. The planar or flat areas 6924a, 6924b of the side wall 6918 are spaced 180° apart as viewed in bottom plan view (FIG. 17), are substantially parallel and equidistant from the cam member axis of rotation CMA, and are located near respective end portions of the recessed regions 6920a, 6920b. Advantageously, in the first, closed position 6998 of blade housing 6800, the planar or flat areas 6924a, 6925b bear against respective ones of the pair of retainer springs 6972a, 6972b of the cam plate 6950 set in the outwardly bowed portions 6970a, 6970b of the side walls 6968a, 6968b of the recess 6964 in the upper surface 6952 of the cam plate 6950. When the cam member 6910 is rotated about the cam member axis of rotation CMA when the cam member 6910 is rotated to the first, closed position 6999, the bearing of the flat areas 6924a, 6924b of the side wall 6918 of the cam member 6910 against the retainer springs 6972a, 6972b causing the cam member 6910 to be set at a specific precise and repeatable rotational orientation, shown schematically, for example, in FIG. 13, with respect to the cam plate 6950 and the blade housing mounting section 6802. As explained below, the bearing of the flat areas 6924a, 6924b of the side wall 6918 of the cam member 6910 against the retainer springs 6972a, 6972b when the cam member 6910 is rotated to the first, closed position 6998 advantageously results in: a) a predetermined, consistent, reproducible and desired split distance value between opposing faces 6825, 6835 of the first and second body portions 6820, 6830 of the blade housing mounting section 6802, namely, split distance D1; and b) a predetermined, consistent, reproducible and desired blade housing diameter, namely, blade housing diameter BHD1 corresponding to the blade housing blade support configuration 6898 having a proper, desired operating or running clearance for the rotary knife blade 6300.

Extending axially from the lower surface 6916 of the cam member 6910 is the downwardly projecting boss 6934. The boss 6934 passes through the central opening 6974 of the cam plate 6950 and extends beyond the lower surface 6916 of the rectangular base 6912 of the cam member 6910. The boss 6934 includes the generally upper cylindrical portion 6935 that is received in the cam plate central opening 6974 and a lower or distal portion 6940 which defines an accessible cam actuator 6943 which allows the cam plate 6910 to be rotated between its first and second positions 6998, 6999. The lower portion 6940 of the boss 6934 extends below the lower surface 6916 and, in one exemplary embodiment, is formed into a hex shaped body 6942. The hex shaped body 6942 is accessible below the cam plate 6950 and functions as the cam actuator 6943. The cam actuator 6943 may be rotated by a conventional ratchet socket or end wrench to move or rotate the cam member 6910 between its first, closed position 6998 and its second, closed position 6999. The cam actuator 6943 rotates about the cam member axis of rotation CMA and the boss 6934 is centered about the center line CLO through the central opening 6974 of the cam plate 6950. The side wall 6936 of the upper cylindrical portion 6935 of the boss 6934 includes the arcuate notch 6938. Viewed in bottom plan view, for example, as seen in FIGS. 21-24, rotation of the cam member 6910 in the counterclockwise direction CCW is limited, as explained previously, to the rotational path of travel RPOT by the interfit of the tab 6978 of the cam plate 6950 into the arcuate notch 6938 of the cam member boss 6934. In one exemplary embodiment, the upper surface 6914 of the cam member 6910 includes a slot 6944 to aid in the assembly of the cam mechanism 6900. Specifically, the slot 6944 allows for easy rotation of the cam member 6910 during assembly such that the cam member 6910 is appropriately seated in the seating region 6966 of the recess 6964 of the cam plate 6950 and the retainer springs 6972a, 6972b of the cam plate 6950 properly bear against the ledges 6922a, 6922b of the cam member 6910 to maintain the cam plate 6910 in place with respect to the cam plate recess 6964.

Extending axially from the planar upper surface 6914 of the rectangular base 6912 of the cam member 6910 are the pair of diagonally spaced apart first and second cam pins 6930, 6932. The first cam pin 6930 is located slightly inwardly of the cam member side wall 6918 near the recess region 6920a of the side wall 6918. The second cam pin 6932 is located slightly inwardly of the cam member side wall 6918 near the recess region 6920b of the side wall 6918. The first cam pin 6930 slidingly engages and moves within the first cam slot 6827 formed in the lower surface 6822 of the first body portion 6820 of the blade housing mounting section 6802. Specifically, the the first cam pin 6930 is constrained by the first cam slot 6827 to move along the generally linear path of travel 6828a defined by the linear portion 6828 of the first cam slot 6827. As noted previously, the first cam slot 6827, if extended along the linear path of travel 6828a, would intersect the blade housing split 6801a. The first cam slot 6827 includes the first end 6827a and the second end 6827b. The second end 6827b of the cam slot 6827 is closer to the blade housing split axis BHSA than the first end 6827a and includes the offset catch portion 6829. The first cam pin 6930 slides along the first cam slot 6827 along the substantially linear path of travel 6928a as the cam member 6910 moves between its first and second positions 6998, 6999. Similarly, the second. cam pin 6932 slidingly engages and moves within the second cam slot 6837 formed in the lower surface 6832 of the second body portion 6830 of the blade housing mounting section 6802. Specifically, the second cam pin 6932 is constrained by the first cam slot 6837 to move along the generally linear path of travel 6838a defined by the linear portion 6838 of the second cam slot 6837. As noted previously, the second cam slot 6837 is transverse to and, if extended along the linear path of travel 6838a, would intersect the blade housing split 6801a. The second cam slot 6837 includes the first end 6827a and the second end 6827b. The second end 6827b of the cam slot 6827 is closer to the blade housing split axis BHSA than the first end 6827a and includes the offset catch portion 6829. The second cam pin 6932 slides along the second cam slot 6837 along the substantially linear path of travel 6938a as the cam member 6910 moves between its first and second positions 6998, 6999.

In the first, closed position 6998 of the cam member 6910, the first cam pin 6930 is positioned at the first end 6827a of the first cam slot 6827 and the second cam pin 6932 is positioned at the first end 6837a of the second cam slot 6837. As the cam actuator 6943 of the cam member 6910 is rotated about the cam member axis of rotation CMA to move the cam plate from the first, closed position 6998 to the second, open position 6999 for blade removal purposes, the first cam pin 6930 moves or slides along the path of travel 6828a moving from the first end 6827a of the first cam slot 6827 to the second end 6827b and is caught and held in the offset catch portion 6829 of the first cam slot 6827. Simultaneously, as the cam actuator 6943 of the cam me giber 6910 is rotated about the cam member axis of rotation CMA to move the cam plate from the first, closed position 6998 to the second, open position 6999 for blade removal purposes, the second cam pin 6932 moves or slides along the path of travel 6838a moving from the first end 6837a of the second cam slot 6837 to the second end 6837b and is caught and held in the offset catch portion 6839 of the second cam slot 6837. Because the respective ends 6827b, 6837b are closer to the blade housing split axis BHSA, the movement of the first and second cam pins 6930, 6932 along the respective paths of travel 6828a, 6838a of the first and second cam slots 6827, 6837 spreads or moves the opposing faces 6825, 6835 of the first and second body portions 6820, 6830 of the blade housing mounting section 6802 apart thereby increasing the diameter of the inner wall 6800a of the blade housing 6800 and thereby increasing the split distance from split distance D1 (blade supporting position 6898) to split distance D2 (blade changing position 6899) allowing the rotary knife blade 6300 to be removed from the blade housing blade support section 6850.

Since the blade housing 6800 is fabricated of a strong and resilient material such as a hardenable grade of alloy steel or a hardenable grade of stainless steel, when moved to an expanded diameter condition (i.e., the blade changing position 6899), the natural tendency for the blade housing 6800 to revert or spring back to its unexpanded or rest position (i.e., the blade supporting position 6898). Thus, the resiliency of the blade housing 6800 would tend to force the cam member 6910 to rotate from the second, open position 6999 back to the first, closed position 6998. Advantageously, to mitigate this effect so that the operator does not have to continuously apply torque to the cam actuator 6943 of the cam member 6910 to maintain the blade housing 6800 in the second, blade changing position 6899, in the second, open position 6999 of the cam member 6910, the cam pins 6930, 6932 are positioned in and stably rest in the respect offset catch portion 6829, 6839 at the second ends 6827b, 6837b of the respective cant slots 6827, 6837. Thus, once the blade housing 6800 is in the second, blade changing position 6899, the blade housing 6800 is stable and stays in its expanded diameter condition without the application of continuous torque to the cam actuator 6943.

One of the advantages of the cam mechanism 6900 is that it provides a simple, durable and repeatable mechanical assembly which allow the operator or maintenance person, by rotating the cam member 6910 to its first, closed position 6998 to return in the diameter of the blade support section 6850 hack to a predetermined, desired blade housing diameter BHD1 corresponding to the blade housing blade support configuration 6898 having a proper, desired operating or running clearance for the rotary knife blade 6300, without the need for further operator or maintenance person adjustment of the blade housing diameter. Stated another way, since the blade housing diameter and the split distance between opposing faces 6825, 6835 of the first and second body portions 6820, 6830 of the blade housing mounting section 6802 are directly proportional, setting the blade housing split distance at a desired value, e.g., the split distance D1, results in the blade support section 6850 of the blade housing 6800 having an outside diameter value that is desired, that is, the blade housing diameter BHD1.

At such time as the rotary knife blade 6300 is replaced and properly positioned in the blade support section 6850 of the blade housing 6800, the operator applies torque to the cam actuator 6943 sufficient to rotate the cam member 6910 from its second, open position 6999 to its first, closed position 6998. Advantageously, in addition to the natural resiliency of the blade housing 6800 which tends to cause the blade to return to its first, closed position 6998, the retainer springs 6972a, 6972b of the cam plate 6950 aid in returning the blade housing 6800 to the first, closed position 6998 and, more specifically, aid in returning the blade housing 6800 to a position wherein: a) the split distance value is consistently and reproducibly the desired split distance D1; and b) the blade housing diameter value is consistently and reproducibly the desired blade housing diameter BHD1. As can best be seen in FIG. 13, in one exemplary embodiment, in the first, closed position 6998 of blade housing 6800, central portions 6973a, 6973b of the retainer springs 6972a, 6972b bear against respective planar or flat areas 6924a, 6925b of the recessed regions 6920a, 6920b of the side wall 6918 of the cam member 6910. When the cam member 6910 is rotated about the cam member axis of rotation CMA when the cam member 6910 is rotated to the first, closed position 6998, the bearing of central portions 6973a, 6973b of the retainer springs 6972a, 6972b against the flat areas 6924a, 6924b of the cam member 6910 cause the cam member 6910 to be set at a specific precise and repeatable rotational orientation, as depicted schematically in FIG. 13, with respect to the cam plate 6950 and the blade housing mounting section 6802. The circumferential extent of a region of contact between the central portion 6973a of the retainer spring 6972a and the flat area 6924a of the cam member side wall 6918 is large. Similarly, the circumferential extent of a region of contact between the central portion 6973b of the retainer spring 6972b and the flat area 6924b of the cam member side wall 6918 is also large. These large circumferential regions of contact advantageously function to essentially firmly lock and maintain the rotational orientation of the cam member 6910 when the cam member is in the first, closed position 6998. Because of the bearing contact between the central portions 6973a, 6973b of the retainer springs 6972a, 6972b against the flat areas 6924a, 6924b of the cam member 6910, in the first, closed position 6998 of the cam member 6910, the retainer springs 6972a, 6972b are under tension and, thus, are slightly bowed or deflected. However, the limited deflection of the retainer springs 6972a, 6972b in the first, closed position 6998 of the cam member 6910 does not deform or permanently bend the retainer springs 6972a, 6972b.

Since the cam member 6910 is always set at the specific predetermined rotational orientation with respect to the cam plate 6950 and the blade housing mounting section 6802, the position of the cam member pins 6930, 6932 of the cam member 6910 are set a specific, predetermined and repeatable locations within their respective cam slots 6827, 6837. That is, because of the bearing of the central portions 6973a, 6973b of the retainer springs 6972a, 6972b in the first, closed position 6998 of the blade housing 6800 against the flat areas 6924a, 6924b of the cam member 6910, the position or location of the cam member pin 6930 at the first end 6827a of the cam slot 6827 of the first body portion 6920 of the blade housing mounting portion 6802 and the position of the cam member pin 6932 at the first end 6837a of the cam slot 6837 of the first body portion 6930 of the blade housing mounting portion 6802 is set precisely, consistently and reproducibly each time the cam member 6910 is rotated to the first, dosed position 6999. The precise and reproducible positioning of the cam member pins 6930, 6932 within their respective cam slots 6927, 6937 resulting from the engagement of the cam plate retainer springs 6972a, 6972b against the respective planar or flat areas 6924a, 6924b of the recessed regions 6920a, 6920b of the side wall 6918 of the cam member 6910 when the blade housing 6800 is in the first, blade supporting position 6898 functions to move the mounting section 6802 of the blade housing 6800 into the same position or configuration every time the cam member 6910 is rotated to its first, closed position 6998.

The bearing of the central portions 6973a, 6973b of the cam plate retainer springs 6972a, 6972b against the respective planar or flat areas 6924a, 6924b of the recessed regions 6920a, 6920b of the side wall 6918 of the cam member 6910 results in a consistent configuration of the mounting section 6802 of the blade housing 6800 and a consistent configuration of the blade support section 6850 of the blade housing 6800 when the cam member 6910 is in the first, closed position 6898. That is, when the cam member 6920 is in the first, closed position 6998, a split distance value between opposing faces 6825, 6835 of the first and second body portions 6820, 6830 of the blade housing mounting section 6802 is precise, consistent, and reproducible, namely, the desired split distance D1. The split distance D1 results in the blade support section 6850 of the blade housing 6800 having the desired diameter value, namely, blade housing diameter BHD1. That is, every time the cam member 6910 is rotated to its first, closed position 6998, the split distance value achieved is substantially identical to the desired split distance value, namely, the split distance D1 and the blade housing diameter achieved is substantially identical to the desired blade housing diameter value, namely, blade housing diameter BHD1. In this condition and configuration of the blade housing 6800, the power operated rotary knife 6000 is ready for operation without the need for further adjustment of the blade housing diameter BHD1 by the operator. Additionally, as mentioned previously, depending upon cutting conditions and maintenance of the power operated rotary knife 6000, the extended wear capability of the double axial blade—blade housing bearing structure 6550 of the assembled blade—blade housing combination 6500 advantageously allows for a "set it and forget it" mode of operation of the power operated rotary knife 6000. That is, once a new or sharpened rotary knife blade 6300 has been inserted into the blade housing blade support section 6850 of the blade housing 6800, as the cam member 6910 is moved to the first, closed position 6998, the blade housing 6800 concurrently moves to its first, blade supporting position 6898 wherein the split distance between the opposing faces 6825, 6835 of the first and second body portions 6820, 6830 of the blade housing mounting section 6802 is consistently and reproducibly is set at the predetermined, desired split distance value, namely, split distance D1 and desired blade housing diameter BHD1. This precise, reproducible positioning and configuration of the blade housing 6800 in the first, blade supporting position 6898 provides for a desired value of operating or running clearance between the annular rotary knife blade 6300 and the blade support section 6850 of the blade housing 6800. Given the extended wear capability of the double axial blade—blade housing bearing structure 6550 of the assembled blade—blade housing combination 6500 and depending on cutting conditions, maintenance of the power operated rotary knife 6000, along with other variables, there may be no need for the operator to make adjustments to blade housing diameter to change operating or running clearance during a work shift thereby allowing for greater operator efficiency and less operator downtime during the work shift, as explained previously.

In one exemplary embodiment, the rectangular base 6912 of the cam member 6910 has length and width dimensions of approximately 0.47 in. and 0.78 in. and a thickness of 0.10 in., while a center to center diagonal distance between the first and second cam pins 6930, 6932 is approximately 0.60 in. In one exemplary embodiment, a center to center distance between the first and second openings 6982a, 6982b of the first and second flanking portions 6980a, 6880b of the cam plate 6950 is approximately 1.22 in., while the thickness or depth of the cam plate 6950 in the first and second flanking portions 6980a, 6880b is approximately 0.17 in. and a diameter of the central opening 6974 of the cam plate is approximately 0.37 in. Again, as noted previously, it is understood, that these dimensions will necessarily change based on the size and configuration, characteristics and parameters of the rotary knife blade to be supported by the blade housing, the blade—blade housing bearing structure, and other parameters and characteristics of the power operated rotary knife 6000 and components thereof.

As used herein, terms of orientation and/or direction such as front, rear, forward, rearward, distal, proximal, distally, proximally, upper, lower, inward, outward, inwardly, outwardly, horizontal, horizontally, vertical, vertically, axial, radial, longitudinal, axially, radially, longitudinally, etc., are provided for convenience purposes and relate generally to the orientation shown in the Figures and/or discussed in the Detailed Description. Such orientation/direction terms are not intended to limit the scope of the present disclosure, this application, and/or the invention or inventions described therein, and/or any of the claims appended hereto. Further, as used herein, the terms comprise, comprises, and comprising are taken to specify the presence of stated features, elements, integers, steps or components, but do not preclude the presence or addition of one or more other features, elements, integers, steps or components.

What have been described above are examples of the present disclosure/invention. It is, of course, not possible to describe every conceivable combination of components, assemblies, or methodologies for purposes of describing the present disclosure/invention, but one of ordinary skill in the art will recognize that many further combinations and permutations of the present disclosure/invention arc possible. Accordingly, the present disclosure/invention is intended to embrace all such alterations, modifications, and variations that fall within the spirit and scope of the appended claims.

What is claimed is:

1. A blade housing assembly for supporting an annular rotary knife blade of a power operated rotary life for rotation about a central axis of rotation, the blade housing assembly comprising:
   a split blade housing including: an annular blade support section, an inner wall of the blade support section defining a blade bearing region; a mounting section extending from the blade support section and including a split extending though the inner wall of the blade support section and defining a split distance between first and second circumferential ends of the inner wall; the mounting section including a first body portion and a second body portion on opposite sides of the split, the first body portion including a first surface and an axially spaced apart second surface including a first cam slot having a first end portion and a spaced apart second end portion; and
   a cam mechanism including: a cam plate bridging the first and second body portions of the mounting section of the split blade housing; and a cam member rotatably supported by the cam plate, the cam member rotatable between a first, closed position and a second, open position and including a base having a first cam pin extending from a first surface of the base and received in the first cam slot of the first body portion of the mounting section of the split blade housing, in the first, closed position of the cam member, the first cam pin is positioned nearer the first end portion of the first cam slot and the split distance between the first and second circumferential ends of the inner wall being a first value, in the second, open position of the cam member, the first cam pin is positioned nearer the second end portion of the first cam slot and the split distance between the first and second circumferential ends of the inner wall being a second value, the second value being greater than the first value.

2. The blade housing assembly of claim 1 wherein the first value of the split distance between the first and second circumferential ends of the inner wall corresponding to a first, blade supporting position of the split blade housing and the second value of the split distance between the first and second circumferential ends of the inner wall corresponding to a second, blade changing position of the split blade housing.

3. The blade housing assembly of claim 1 wherein the inner wall of the blade support section of the split blade housing is centered about a blade housing center line and further wherein the second end portion of the first cam slot is closer to the split than the first end portion of the first cam slot and, in the first, closed position of the cam member, the first cam pin is positioned at the first end portion of the first cam slot and, in the second, open position of the cam member, the first cam pin is positioned at the second end portion of the first cam slot.

4. The blade housing assembly of claim 1 wherein the cam plate includes an opening extending through the cam plate and the base of the cam member includes a first surface and an axially spaced apart second surface and a boss extending from the second surface and rotatably received in the opening of the cam plate, the boss including an actuator for rotating the cam member between the first, closed position and the second, open position.

5. The blade housing assembly of claim 1 wherein the second body portion of the mounting section of the blade housing includes a first surface and an axially spaced apart second surface, the second surface including a second cam slot having a first end portion and a spaced apart second end portion and further wherein the cam member includes a second cam pin extending from the first surface of the base and received in the second cam slot of the second body portion of the mounting section of the split blade housing, in the first, closed position of the cam member, the second cam pin is positioned nearer the first end portion of the second cam slot and in the second, open position of the cam member, the second cam pin is positioned nearer the second end portion of the second cam slot.

6. The blade housing assembly of claim 5 wherein the second end portion of the second cam slot is closer to the split than the first end portion of the second cam slot and in the first, closed position of the cam member, the second cam pin is positioned at the first end portion of the second cam slot and in the second, open position of the cam member, the second cam pin is positioned at the second end portion of the second cam slot.

7. The blade housing assembly of claim 5 wherein the cam mechanism further includes first and second fasteners and the cam plate includes an upper surface and an axially spaced apart lower surface, a recess in the upper surface and first and second flanking portions on either side of the recess, the first flanking portion including a first opening and the second flanking portion including a second opening, the first body portion of the split blade housing including a first mounting slot and the second body portion of the split blade housing including a second mounting slot and wherein the first fastener extends through the first opening in the first flanking portion of the cam plate and extends through the first mounting slot of the first body portion of the split blade housing and the second fastener extends through the second opening in the second flanking portion of the cam plate and extends through the second mounting slot of the second body portion of the split blade housing to couple the cam mechanism to the split blade housing.

8. A blade housing assembly for supporting an annular rotary knife blade of a power operated rotary knife for rotation about a central axis of rotation, the blade housing assembly comprising:
   a split blade housing including: an annular blade support section having an inner wall and a radially spaced apart outer wall and a first end and an axially spaced apart second end, the inner wall of the blade support section defining a blade bearing region; a mounting section extending from the blade support section and including a split extending through the inner wall of the blade support section and defining a split distance between first and second circumferential ends of the inner wall; the mounting section including a first body portion and a second body portion on opposite sides of the split, the first body portion including a first surface and an axially spaced apart second surface including a first cam slot having a first end portion and a spaced apart second end portion, the second body portion including a first surface and an axially spaced apart second surface including a second cam slot having a first end portion and a spaced apart second end portion; and a cam mechanism including: a cam plate bridging the first and second body portions of the mounting section of the split blade housing; and a cam member rotatably supported by the cam plate, the cam member rotatable between a first, closed position and a second, open position and including a base having a first cam pin extending from the cam plate and received in the first cam slot of the first body portion of the mounting section of the split blade housing and a second cam pin extending from the cam plate and received in the second cam slot of the second body portion of the mounting section of the split blade housing, in the first, closed position of the cam member, the first cam pin is positioned nearer the first end portion of the first cam slot, the second cam pin is positioned nearer the first end portion of the second cam slot and the split distance between the first and second circumferential ends of the inner wall being a first value, in the second, open position of the cam member, the first cam pin is positioned nearer the second end portion of the first cam slot, the second cam pin is positioned nearer the second end portion of the second cam slot and the split distance between the first and second circumferential ends of the inner wall being a second value, the second value being greater than the first value.

9. The blade housing assembly of claim 8 wherein the first value of the split distance between the first and second circumferential ends of the inner wall corresponding to a first, blade supporting position of the split blade housing and the second value of the split distance between the first and second circumferential ends of the inner wall corresponding to a second, blade changing position of the split blade housing.

10. The blade housing assembly of claim 8 wherein the inner wall of the blade support section of the split blade housing is centered about a blade housing center line and further wherein the second end portion of the first cam slot is closer to the split than the first end portion of the first cam slot and the second end portion of the second cam slot is closer to the split than the first end portion of the second cam slot and in the first, closed position of the cam member, the first cam pin is positioned at the first end portion of the first cam slot and the second cam pin is positioned at the first end portion of the second cam slot and, in the second, open position of the cam member, the first cam pin is positioned at the second end portion of the first cam slot and the second cam pin is positioned at the second end portion of the second cam slot.

11. The blade housing assembly of claim 8 wherein the cam plate includes an opening extending through the cam plate and the base of the cam member includes a first surface and an axially spaced apart second surface and a boss extending from the second surface and rotatably received in the opening of the cam plate, the boss including an actuator for rotating the cam member between the first, closed position and the second, open position.

12. The blade housing assembly of claim 8 wherein the cam mechanism further includes first and second fasteners and the cam plate includes an upper surface and an axially spaced apart lower surface, a recess in the upper surface and first and second flanking portions on either side of the recess, the first flanking portion including a first opening and the second flanking portion including a second opening, the first body portion of the split blade housing including a first mounting slot and the second body portion of the split blade housing including a second mounting slot and wherein the first fastener extends through the first opening in the first flanking portion of the cam plate and extends through the first mounting slot of the first body portion of the split blade housing and the second fastener extends through the second opening in the second flanking portion of the cam plate and extends through the second mounting slot of the second body portion of the split blade housing to couple the cam mechanism to the split blade housing.

13. A power operated rotary knife comprising:
an annular rotary knife blade supported for rotation about a central axis of rotation;
an elongated handle assembly extending along a longitudinal axis;
a frame body coupled to a distal end of the elongated handle assembly, the frame body including a mounting pedestal; and
a blade housing assembly coupled to the frame body and supporting the annular rotary knife blade for rotation about the central axis of rotation, the blade housing assembly including:
a split blade housing including: an annular blade support section, an inner wall of the blade support section defining a blade bearing region; a mounting section extending from the blade support section and including a split extending through the inner wall of the blade support section and defining a split distance between first and second circumferential ends of the inner wall; the mounting section including a first body portion and a second body portion on opposite sides of the split, the first body portion including a first surface and an axially spaced apart second surface including a first cam slot having a first end portion and a spaced apart second end portion; and
a cam mechanism including: a cam plate bridging the first and second body portions of the mounting section of the split blade housing; and a cam member rotatably supported by the cam plate, the cam member rotatable between a first, closed position and a second, open position and including a base having a first cam pin extending from a first surface of the base and received in the first cam slot of the first body portion of the mounting section of the split blade housing, in the first, closed position of the cam member, the first cam pin is positioned nearer the first end portion of the first cam slot and the split distance between the first and second circumferential ends of the inner wall being a first value, in the second, open position of the cam member, the first cam pin is positioned nearer the second end portion of the first cam slot and the split distance between the first and second circumferential ends of the inner wall being a second value, the second value being greater than the first value frame body, the cam mechanism securing the mounting section of the split blade housing to the mounting pedestal of the frame body.

14. The power operated rotary knife of claim 13 wherein the mounting pedestal of the frame body further includes first and second threaded openings and the cam mechanism further includes first and second threaded fasteners and the cam plate includes a first opening and a second opening, the first body portion of the split blade housing including a first mounting slot and the second body portion of the split blade housing including a second mounting slot and wherein the first fastener extends through the first opening of the cam plate and extends through the first mounting slot of the first body portion of the split blade housing and threads into the first threaded opening of the mounting pedestal of the frame body and the second fastener extends through the second opening of the cam plate and extends through the second mounting slot of the second body portion of the split blade housing to secure the cam mechanism and the split blade housing to the frame body.

15. The power operated rotary knife of claim 13 wherein the first value of the split distance between the first and second circumferential ends of the inner wall corresponding to a. first, blade supporting position of the split blade housing and the second value of the split distance between the first and second circumferential ends of the inner wall corresponding to a second, blade changing position of the split blade housing.

16. The power operated rotary knife of claim 13 wherein the inner wall of the blade support section of the split blade housing is centered about a blade housing center line and further wherein the second end portion of the first cam slot is closer to the split than the first end portion of the first cam slot and, in the first, closed position of the cam member, the first cam pin is positioned at the first end portion of the first cam slot and, in the second, open position of the cam member, the first cam pin is positioned at the second end portion of the first cam slot.

17. The power operated rotary knife of claim 13 wherein the cam plate includes an opening extending through the cam plate and the base of the cam member includes a first surface and an axially spaced apart second surface and a boss extending from the second surface and rotatably received in the opening of the cam plate, the boss including an actuator for rotating the cam member between the first, closed position and the second, open position.

18. The power operated rotary knife of claim 13 wherein the second body portion of the mounting section of the blade housing includes a first surface and an axially spaced apart second surface, the second surface including a second cam slot having a first end portion and a spaced apart second end portion and further wherein the cam member includes a second cam pin extending from the first surface of the base and received in the second cane slot of the second body portion of the mounting section of the split blade housing, in the first, closed position of the cam member, the second cam pin is positioned nearer the first end portion of the second cam slot and in the second, open position of the cam member, the second cam pin is positioned nearer the second end portion of the second cam slot.

19. The power operated rotary knife of claim 18 wherein the second end portion of the second cam slot is closer to the split than the first end portion of the second cam slot and, in the first, closed position of the cam member, the second cam pin is positioned at the first end portion of the second cam slot and in the second, open position of the cam member, the second cam pin is positioned at the second end portion of the second cam slot.

20. The power operated rotary of claim 13 wherein the mounting pedestal of the frame body further includes first and second threaded openings, the cam mechanism further includes first and second threaded fasteners and the cam plate includes a first surface and an axially spaced apart second surface, a recess in the first surface and first and second flanking portions on either side of the recess, the first flanking portion including a first opening and the second flanking portion including a second opening, the first body portion of the split blade housing including a first mounting slot and the second body portion of the split blade housing including a second mounting slot and wherein the first fastener extends through the first opening in the first flanking portion of the cam plate and extends through the first mounting slot of the first body portion of the split blade housing and threads into the first threaded opening of the frame body and the second fastener extends through the second opening in the second flanking portion of the cam plate and extends through the second mounting slot of the second body portion of the split blade housing and threads into the second threaded opening of the frame body to secure the cam mechanism and the split blade housing, the base of the cam member being received in the recess of the first surface of the cam plate.

* * * * *